United States Patent
Amalfitano et al.

(10) Patent No.: US 6,946,126 B2
(45) Date of Patent: Sep. 20, 2005

(54) REPLICATING ADENOVIRUS VECTORS

(75) Inventors: Andrea Amalfitano, Durham, NC (US); Bradley L. Hodges, Milford, MA (US); Dwight D. Koeberl, Durham, NC (US)

(73) Assignee: Duke University, Durham, NC (US)

( * ) Notice: Subject to any disclaimer, the term of this patent is extended or adjusted under 35 U.S.C. 154(b) by 279 days.

(21) Appl. No.: 10/159,946

(22) Filed: May 30, 2002

(65) Prior Publication Data

US 2003/0109472 A1 Jun. 12, 2003

Related U.S. Application Data

(60) Provisional application No. 60/295,914, filed on Jun. 4, 2001.

(51) Int. Cl.$^7$ .......................... A61K 48/00; C12N 5/10; C12N 15/861; C12N 15/63
(52) U.S. Cl. .................... 424/93.2; 424/93.1; 424/93.6; 435/320.1; 435/325; 435/69.1; 435/455; 435/456; 435/457; 435/235.1; 536/23.1; 536/23.72; 536/23.2; 536/24.1
(58) Field of Search .............................. 435/320.1, 325, 435/69.1, 455, 456, 457, 235.1; 536/23.1, 23.72, 23.2, 24.1; 424/93.1, 93.2, 93.6

(56) References Cited

U.S. PATENT DOCUMENTS 6,328,958 B1 * 12/2001 Amalfitano et al. ....... 424/93.2

* cited by examiner

*Primary Examiner*—David Guzo
(74) *Attorney, Agent, or Firm*—Myers Bigel Sibley & Sajovec, P.A.

(57) ABSTRACT

The present invention provides replicating [100K-] adenovirus vectors that have an impairment in 100K activity. In particular preferred embodiments, the impairment is the result of a deletion in the 100K coding region of the adenovirus vector genome. It is further preferred that the adenovirus produces the E1 gene products. In an alternate embodiment, the adenovirus produces the E1a gene products, but has an impairment in the E1b coding region, such that replication of the virus is limited to p53– cells. Also described are methods of making and administering the inventive adenovirus vectors to a cell or to a subject. Further provided is use of the inventive [100K-] Ad vectors as a helper virus for the production of vector stocks of adeno-associated virus.

70 Claims, 10 Drawing Sheets

A.

| H5ts116 infection @ | 32.0°C | 39.0°C |
|---|---|---|
| 293 cells (E1+) | +++ | 0 |
| K-16 cells (E1+, 100K+) | +++ | +++ |

0 = no cytopthic effect    +++ = all cells undergo cytopathic effect

B
293  K16  control
-100K

C
293  K16
-100K
-28s rRNA
-18s rRNA

Figure 1.

SEQUENCE LISTING

<160> NUMBER OF SEQ ID NOS: 6
<210> SEQ ID NO 1
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 1
cggaattcga tcatggagtc agtcgag                27

<210> SEQ ID NO 2
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 2
gcctctagag tcccatctac ggttggg                27

<210> SEQ ID NO 3
<211> LENGTH: 22

```
-continued

<212> TYPE: DNA
<213> ORGANISM: Artificial sequence
<220> FEATURE:
<223> OTHER INFORMATION: Synthetic oligonucleotide

<400> SEQUENCE: 3
ggtagcacca ctgcagagct tc                                              22

<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 4
ggtcacaagg gcgtctccaa g                                               21

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
accacagtcc atcggatcac                                                 20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
tccaccaccc tgttgctgta                                                 20
```

REPLICATING ADENOVIRUS VECTORS

RELATED APPLICATION INFORMATION

This application claims the benefit of U.S. Provisional Application No. 60/295,914, filed Jun. 4, 2001, which is incorporated by reference herein in its entirety.

STATEMENT OF FEDERAL SUPPORT

The present invention was made, in part, with the support of grant number DK 52925 from the National Institutes of Health. The United States government has certain rights to this invention.

FIELD OF THE INVENTION

The present invention relates to reagents and methods for gene delivery in vitro or in vivo. More particularly, the present invention relates to improved adenovirus-based gene delivery vectors.

BACKGROUND OF THE INVENTION

Helper-virus independent, E1 deleted adenovirus (Ad) based gene transfer vectors exhibit many positive attributes, including a large transgene encoding capacity, a relative ease of high titer production to clinical grades, and the ability to infect a wide range of tissue types. Despite the fact that [E1−]Ad vectors are significantly blocked in their ability to replicate (relative to a wild-type Ad), low level replication and/or gene expression derived from [E1−]Ad vectors can limit their usefulness (Amalfitano et al., (1998) *J. Virology* 72:926; Steinwaerder et al., (2000) *Hum. Gene Ther.* 11:1933). To overcome this problem, it has previously been demonstrated that [E1−]Ad vectors incorporating additional deletions in the Ad E2b genes (polymerase and/or pTP) rendered [E1−,E2b−]Ad vectors truly replication incompetent (Amalfitano et al., (1998) *J. Virology* 72:926; Hodges et al., (2000) *J. Gene Medicine* 2:250; Hu et al., (1999) *Hum. Gene Ther.* 10:355). As a result, [E1−,E2b−]Ad vector derived late gene expression was also significantly diminished, since Ad late gene expression is only initiated after Ad genome replication has occurred (Thomas et al., (1980) *Cell* 22:523).

Despite the problems associated with Ad replication, an Ad vector that can replicate its genome to high levels in infected cells would be valuable in certain applications. For example, this feature may be capitalized to amplify expression of a transgene encoded by the vector, and/or to induce cytopathic effects as a consequence of high level Ad replication and/or infectious virus production. For example, [E1a+,E1b−] Ad vectors have been described; the E1b deletion restricts E1a dependent vector replication (and generation of infectious vector) to cancer cells, resulting in their death (Bischoff et al., (1996) *Science* 274:373; Heise et al., (1997) *Nature Med.* 3:639). There is evidence, however, that [E1a+,E1b−]Ad vectors can also replicate in non-cancerous cells, potentially limiting the benefit/risk ratio of [E1a+,E1b−]Ad based cancer therapies (Rothmann et al., *J. Virology* 72:9470).

In a recent attempt to address the latter concerns, Ad vectors have been developed that are protease deleted (Oualikene et al., (2000) *J. Virology* 11:1341). Protease deleted [E1+]Ad viruses can replicate, but are blocked in their ability to produce infectious virus, due to inadequate maturation of viral capsid proteins during the late phase of the Ad life cycle. Importantly, however, [E1+]Ad vectors having deletions in both the E1b and protease regions are fully capable of producing wild-type levels of the Ad late genes once replication has occurred (Oualikene et al., (2000) *J. Virology* 11:1341). The late genes are numerous and include the hexon, 100K, penton, and fiber proteins. The toxicity normally associated with the expression of these proteins (particularly penton) may limit the overall usefulness of both [E1a+,E1b−]Ad and protease deleted [E1+]Ad vectors.

Accordingly, there is a need in the art for improved Ad vectors, in particular, improved replicating Ad vectors.

SUMMARY OF THE INVENTION

It is with the foregoing considerations in mind that the present inventors targeted the adenovirus 100K gene. After Ad genomic replication occurs, transcription is initiated from the major late promoter (MLP), which results in the generation of the L4 transcript, which encodes the Ad 100K protein. The 100K gene encompasses fully 10% of the Ad genome, reflective of the important role 100K plays in various aspects of the Ad life cycle. Functions of the 100K protein include the transport of newly synthesized hexon monomers (the major structural protein of the Ad capsid) from the cytoplasm to the nucleus, and trimerization of hexon monomers (Cepko et al., (1983) *Virology* 129:137). 100K also acts as a "scaffolding platform" for the assembly of virus capsids, although the 100K protein has not been found to be physically incorporated into mature Ad capsids (Morin et al., (1986) *Virology* 152:11). 100K can also interact with a number of RNA transcripts, both vector and host cell derived, preferentially allowing for translation of Ad derived late gene transcripts (Adam et al., (1987) *J. Virology* 61:3276; Mathews, (1990) *Enzyme* 44:250; Riley et al., (1993) *J. Virology* 67:3586).

The present invention provides replicating [100K−] Ad vectors. The Ad vectors of the invention may advantageously be employed for a variety of purposes, e.g., for any purpose in which it is desirable to transfer a nucleotide sequence of interest into a cell in vitro, ex vivo, or in vivo.

In one particular embodiment, the Ad vector has E1 activity, but is defective (i.e., impaired) at the 100K locus (i.e., an [E1+, 100K−] virus that does not produce a functional 100K protein). In embodiments of the invention, the 100K locus is defective due to a deletion in the coding sequence for the Ad 100K protein. As described in more detail below, the inventive [E1+, 100K−] Ad is competent for replication of the viral genome, but is impaired with respect to propagation or spread (i.e., the ability to package new virus and infect other cells is reduced or eliminated).

In another particular embodiment, the present invention provides a recombinant Ad vector, comprising an Ad vector genome (optionally, packaged within an Ad capsid), wherein: (a) the Ad vector genome comprises a functional E1 coding region; and (b) the Ad vector genome comprises a mutation in the 100K coding region, such that reduced levels of functional 100K protein (e.g., decreased by at least about 50%, 75%, 80%, 90%, 95%, 98%, 99% or more as compared with a wild-type or otherwise [100K+] Ad) are expressed from the Ad vector genome.

The [E1+, 100K−]Ad vectors of the invention may be used for therapeutic purposes, for example, to administer a heterologous nucleotide sequence to a subject that encodes a therapeutic polypeptide or RNA (as described below). The [E1+, 100K−]Ad vector may be administered directly to the subject, or to a cell ex vivo, and the cell then administered to the subject.

The inventive replicating Ad vectors may advantageously amplify transgene expression in infected cells. In the case of a replication-defective vector (e.g., E1–), all transgene expression is derived from the genomes present in the introduced virions. In contrast, for an [E1+,100K–] Ad vector, transgene expression would not only occur from the genomes present in the infecting vector, but also from additional copies as a result of subsequent replication of the genome. There would be a simultaneous amplification of the foreign nucleic acid sequence (i.e., a transgene) incorporated into the Ad genome. Amplification may result in higher transgene expression in the target cell. Thus, lower doses of the [E1+, 100K–] virus may be administered as compared with non-replicating Ad vectors to achieve similar levels of gene expression. This feature of the replicating [E1+, 100K–] Ad vector may further be beneficial for expressing a heterologous nucleotide sequence of interest in a cell or tissue that has low levels of the Ad receptor (i.e., the coxsackie-adenovirus receptor [CAR]). Such tissues may include skeletal muscle, hematopoietic stem cells, particular cancer and tumor cells and, in some species (e.g., human), liver.

Moreover, the inventive [100K–] vectors are impaired in their ability to produce new virions, possibly due to reduced accumulation of particular viral late proteins (e.g., hexon, fiber and/or penton), and may therefore have reduced cytopathic effects (CPE) in target cells as compared with first generation [E1–, 100K+] Ad vectors. Reduced CPE may further result in longer transgene persistence and expression as compared with first-generation Ad vectors. The reduction in the accumulation of particular Ad late proteins may be due to decreased transcription of the Ad late genes and/or decreased translation of the Ad late gene transcripts as a result of impaired levels of functional 100K protein. Alternatively, or additionally, there may be an increased rate of capsid protein turnover and/or reduction in capsid assembly because of decreased levels of functional 100K protein.

A further use of the inventive [E1+, 100K–] Ad vectors is in immunization strategies. An [E1+, 100K–] Ad vector that expresses an immunogenic polypeptide may be administered to a subject in vivo to produce an immune response in the subject against the immunogen. Alternatively, the Ad vector may be introduced into a cell ex vivo, and the cell administered to the subject. According to this particular embodiment, preferably the cell is an antigen presenting cell (APC), more preferably a dendritic cell. The inventive [E1+, 100K–] Ad vectors may be used to deliver an immunogen, for example, from a pathogen (e.g., viral, bacterial, fungal or protozoan pathogenic agents).

As a further aspect, the replicating [E1+, 100K–] Ad vectors of the invention find use in methods of cancer therapy. As one embodiment, the inventive vector may be used in methods of cancer immunotherapy, e.g., may encode a cancer cell antigen or other immunogen that induces an immune response against cancer cells. Alternatively, or additionally, the inventive [E1+, 100K–] vectors may be used to deliver an anti-cancer agent (e.g., an anticancer polypeptide or RNA).

The viruses of the invention may have a substantially reduced propensity to spread to non-cancerous cells due to the defect in the 100K locus.

In embodiments of the invention, the [E1+, 100K–] Ad vector is administered directly into the cancerous tissue (e.g., by injection into a tumor) so as to give high localized expression of the anti-cancer agent and/or immunogen.

In other embodiments, the inventive Ad vector further has a mutation in the E1b region of the Ad genome (i.e., is [E1b–]), such that the Ad vector produce reduced E1b activity (i.e., production of the p55 gene product encoded by the E1b region is decreased by at least about 50%, 75%, 80%, 90%, 95%, 98%, 99% or more as compared with a wild-type or otherwise [E1b+] Ad). Such mutations in the Ad E1b locus are known in the art, see e.g., Steinwaerder et al., (2001) *Nature Med.* 7:240; Bischoff et al., (1996) *Science* 274:373); U.S. Pat. No. 6,080,578; U.S. Pat. No. 5,846,945). [E1a+, E1b–, 100K–] Ad vectors may advantageously have a reduced ability to replicate in non-cancerous (i.e., p53+ cells), but to replicate in p53– cancer cells.

[E1a–, E1b–, 100K–] Ad vectors are also useful in methods of cancer immunotherapy; in particular embodiments, [E1a+, E1b–, 100K–] Ad are employed because of the potential for transgene amplification in infected cancer cells, as described above.

As an alternative method for restricting Ad replication to cancer cells, the heterologous nucleotide sequence or the E1 sequences (E1a and/or E1b) may be operatively associated with a cancer cell specific transcriptional regulatory sequence (e.g., a promoter, such as a prostate cancer specific promoter and the like).

As still a further alternative, the Ad vector may be modified to be "targeted" to cancer cells. Targeted Ad are known in the art (see, e.g., Douglas et al., (1996) Nature Biotechnology 14:1574; U.S. Pat. No. 5,922,315 to Roy et al.; U.S. Pat. No. 5,770,442 to Wickham et al.; and/or U.S. Pat. No. 5,712,136 to Wickham et al.).

As a still further alternative, the [E1+, 100K–] Ad vectors of the invention find use in in vitro systems for producing recombinant polypeptides. Amplification of the viral genome may advantageously produce high level expression of a recombinant polypeptide of interest in a cell culture system. This embodiment may be practiced to express any polypeptide of interest, including therapeutic polypeptides or industrial polypeptides (e.g., industrial enzymes).

As still a further aspect, the present invention may be employed to provide an improved helper virus for producing adeno-associated virus (MV) vector stocks. A helper [E1+, 100K–] Ad may result in AAV preparations with lower levels of contamination by Ad particles as well as the Ad late proteins, e.g., hexon, penton, fiber, which are toxic to mammalian cells. In particular, a hybrid [E1+, 100K–] Ad helper that expresses the MV rep and/or cap proteins may provide a simplified protocol and better yield than current MV production schemes.

These and other aspects of the present invention are set forth in more detail in the following description of the invention.

BRIEF DESCRIPTION OF THE DRAWINGS

FIG. 1A shows cytopathic effects in infected cells. The mutant virus H5ts116 was utilized to infect various G-418 resistant cell lines at the permissive temperature of 32° C., or the non-permissive temperature of 39° C. The K-16 cell line supported growth of the virus (as evidenced by the onset of cytopathic effect "+++") at both temperatures.

FIG. 1B demonstrates detection of 100K specific DNA sequences within K-16 cells. A 100K specific PCR product at ~2.3 kb was only detected when DNA isolated from the G-418 resistant K-16 cells was utilized as template. The first lane contains a 1 kb DNA ladder, while the control lane utilized pcDNA3/100K as a positive control template.

FIG. 1C shows detection of 100K specific RNA sequences within K-16 cells. A 100K specific mRNA was detected only in RNA isolated from the G-418 resistant K-16 cells. The lower half of the figure depicts the amounts of RNA loaded in the gel prior to transfer to the nylon membrane, demonstrating that both samples contained equal amounts of intact RNA.

Figure 2A:
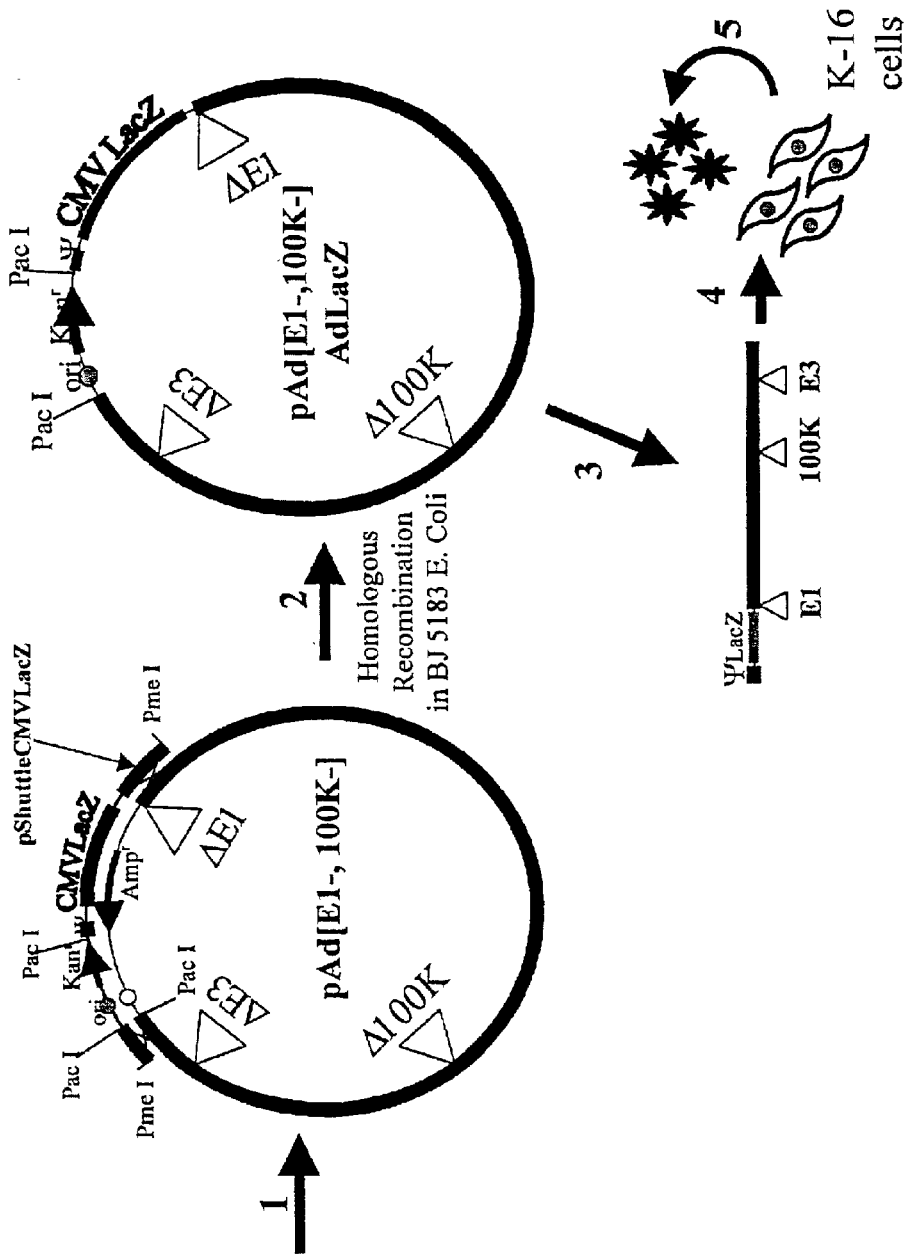

FIG. 2A demonstrates assembly of 100K deleted Ad vectors by homologous recombination in bacterial plasmids. Construction of [E1–, E3–, 100K–]AdLacZ: 1: Co-electroporate linearized pShuttleCMVLacZ with p[E1–, E3–, 100K–]Ad into BJ5183 E. coli. 2: Screen kanamycin resistant colonies for identification of clones containing recombinant pAd[E1–,E3–,100K–]AdLacZ plasmid. 3: Linearize the p[E1–,E3–,100K–] AdLacZ plasmid with Pac I, releasing the Ad ITR elements. 4: Transfect Pac I linearized p[E1–,E3–,100K–]AdLacZ into K-16 cells for virus growth. 5: Serially propagate virus for conventional Ad vector amplification and purification.

Figure 2B:
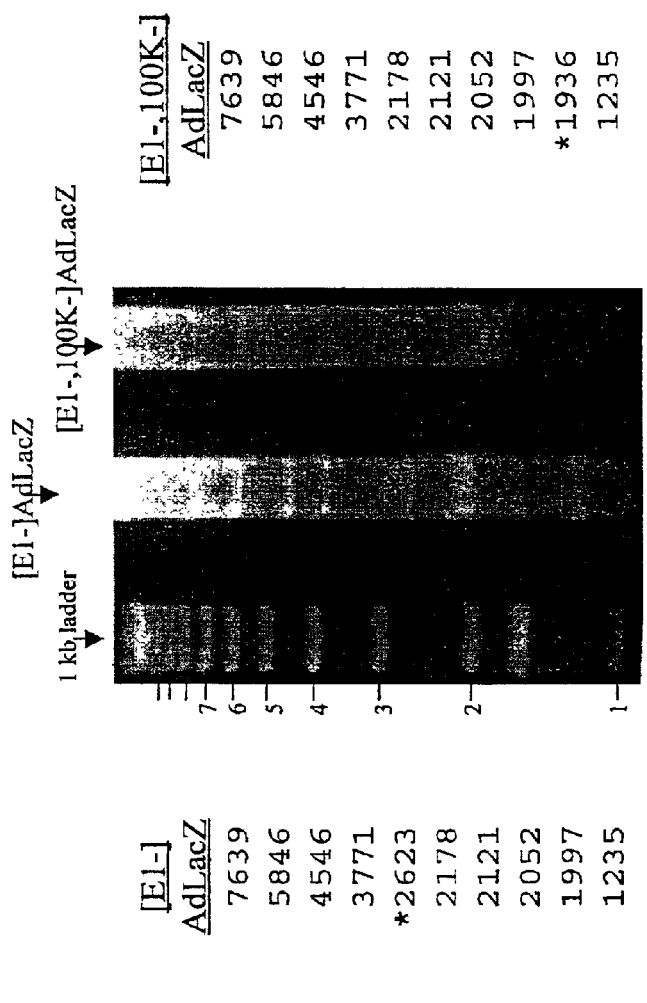

FIG. 2B provides confirmation of [E1–,E3–,100K–] AdLacZ genome integrity. K-16 cells were identically infected at a MOI of 5 with each of the indicated vectors, total DNA was harvested 20 hours after infection, and nearly equivalent amounts were digested with EcoRV. The genomes of the two vectors are identical except for the altered migration of the indicated subfragment (*) in the [E1–,E3–,100K–]AdLacZ vector, the latter fragment encompasses the 100K deletion.

Figure 3:
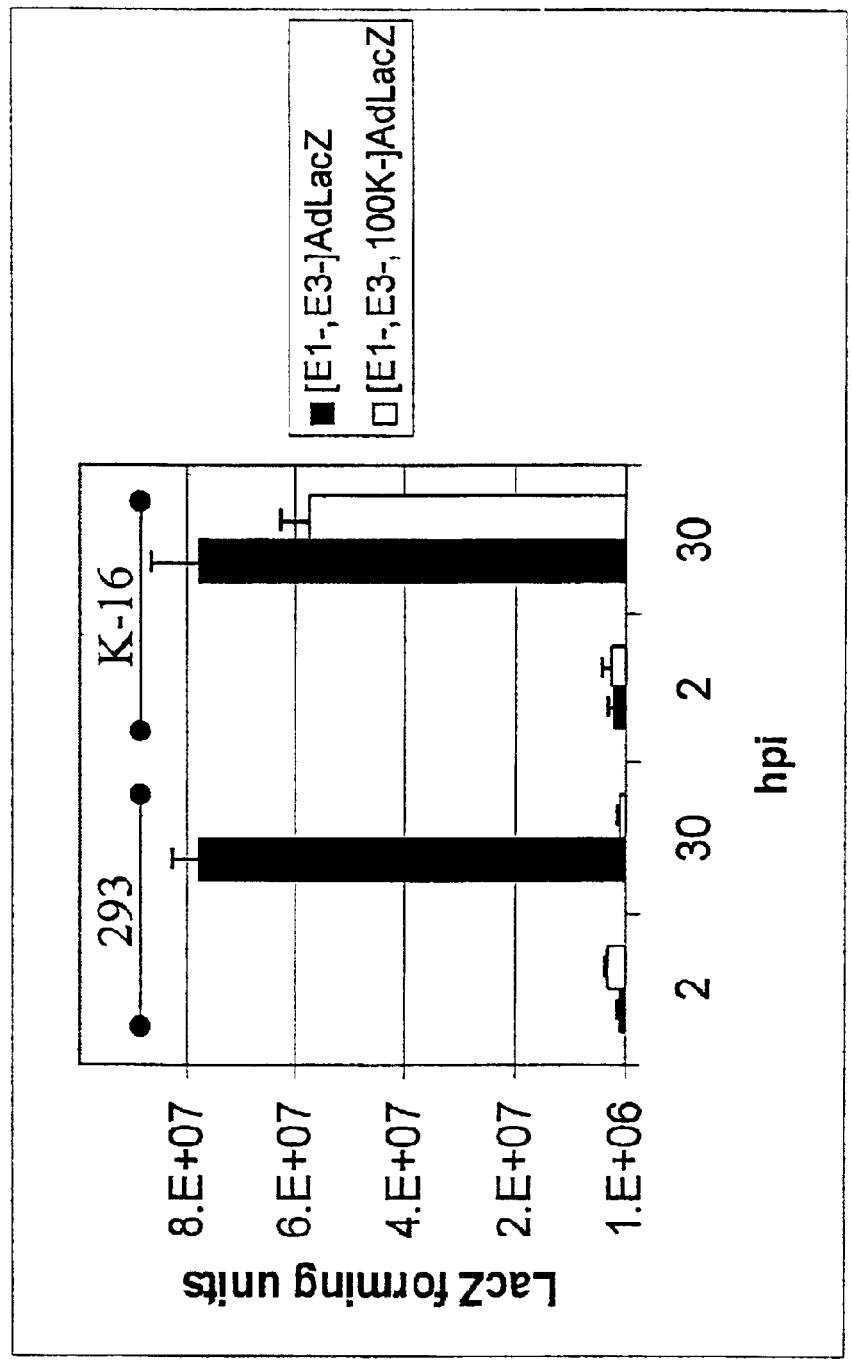

FIG. 3 shows growth of modified vectors occurs only in 100K– transcomplementing cell lines. The indicated cell lines were infected at an MOI=5, and incubated for the indicated time periods. Infectious virus (as determined by assessing total LacZ transducing units yielded from two identical infections) during viral eclipse (2 hpi) and after virus replication (30 hpi) were compared.

Figure 4:
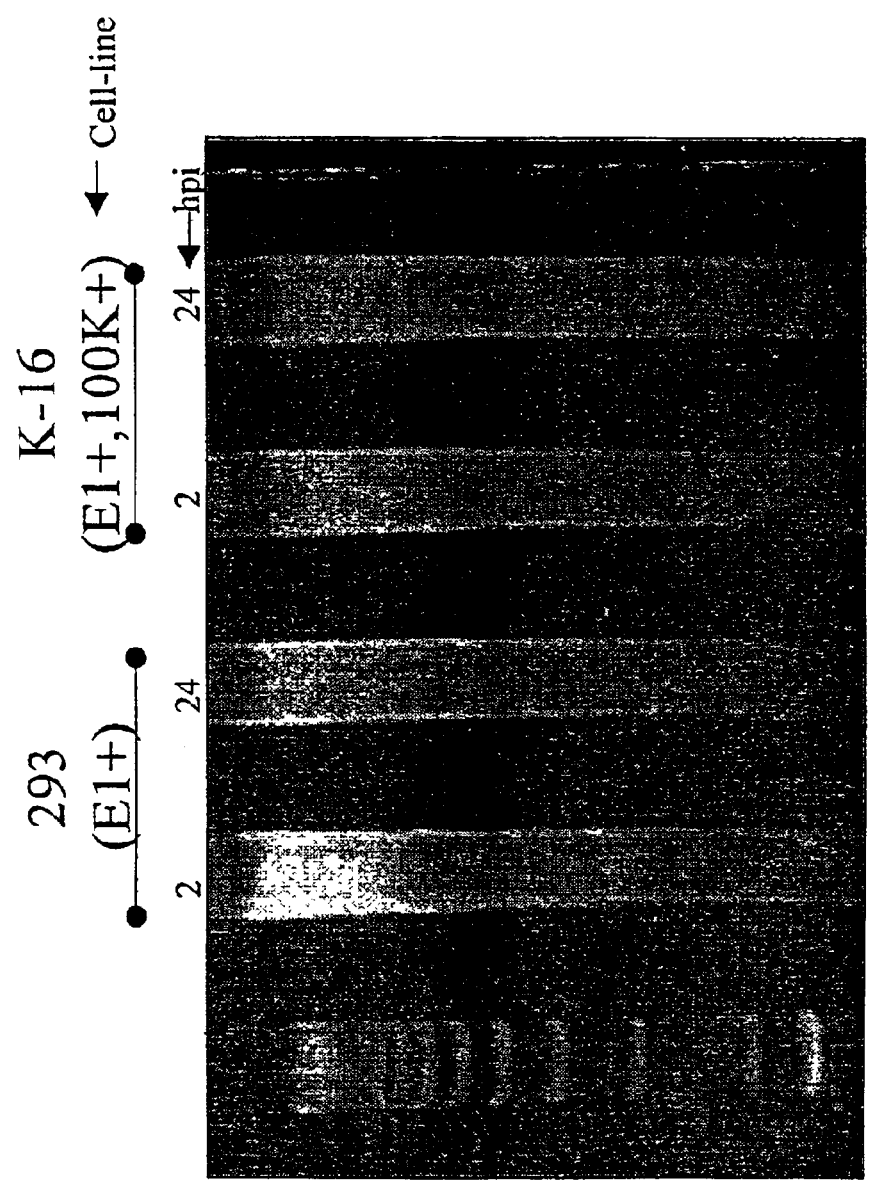

FIG. 4 replication of [E1–,E3–,100K–]AdLacZ in the presence of E1. 293 or K-16 cells were infected at an MOI of 5 with [E1–,E3–,100K–] AdLacZ, and total DNA was electrophoretically separated and visualized after ethidium bromide staining of the gel.

Figure 5A:
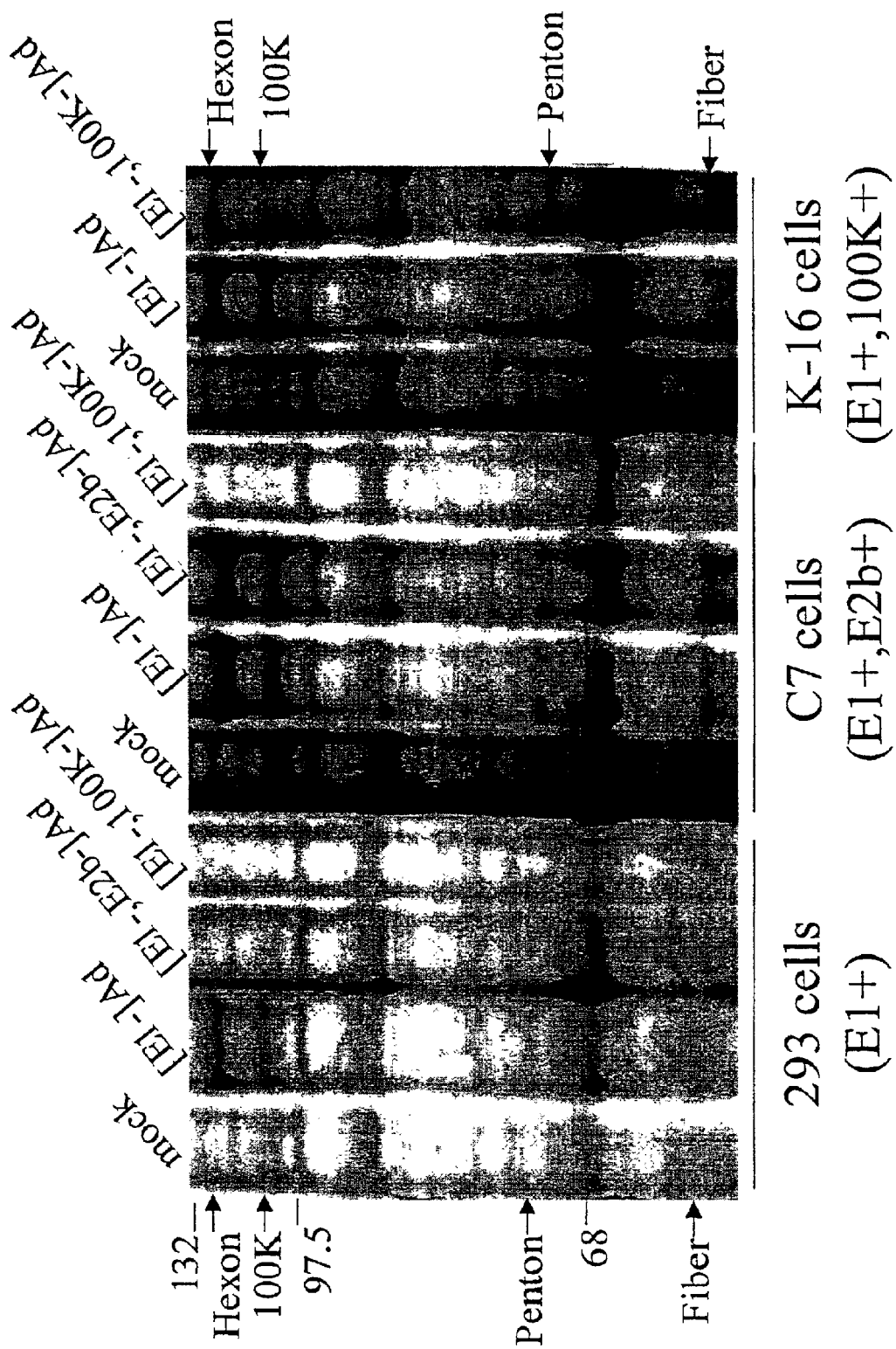

FIG. 5A shows the results of [E1–,E3–,100K–] Ad late gene expression analysis. The indicated cell lines were infected at a MOI of 5 with the respective vectors. Duplicate infections were carried out, and proteins were either not labeled, or $^{35}$S-methionine radio-labeled (see FIG. 5B). Identical amounts of all proteins derived from the infections were extracted, electrophoretically separated, and visualized by Coomassie staining of the gels. The location of the Ad late proteins hexon, 100K, penton, and fiber are indicated.

Figure 5B:
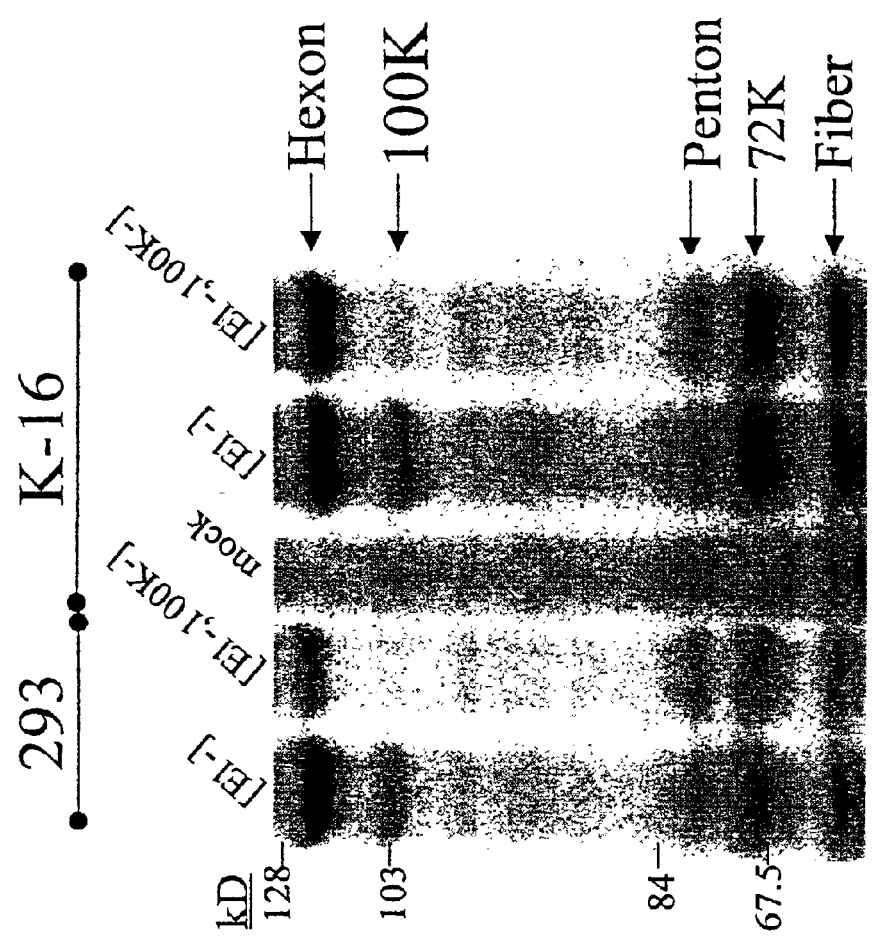

FIG. 5B shows the results of [E1–,E3–,100K–] Ad late gene expression analysis. The indicated cell lines were infected at a MOI of 5 with the respective vectors. Duplicate infections were carried out, and proteins were either not labeled, or $^{35}$S-methionine radio-labeled. Identical amounts of all proteins derived from the infections were extracted, electrophoretically separated, and visualized by autoradiography. The location of the Ad late proteins hexon, 100K, penton, and fiber are indicated.

Figure 6A:
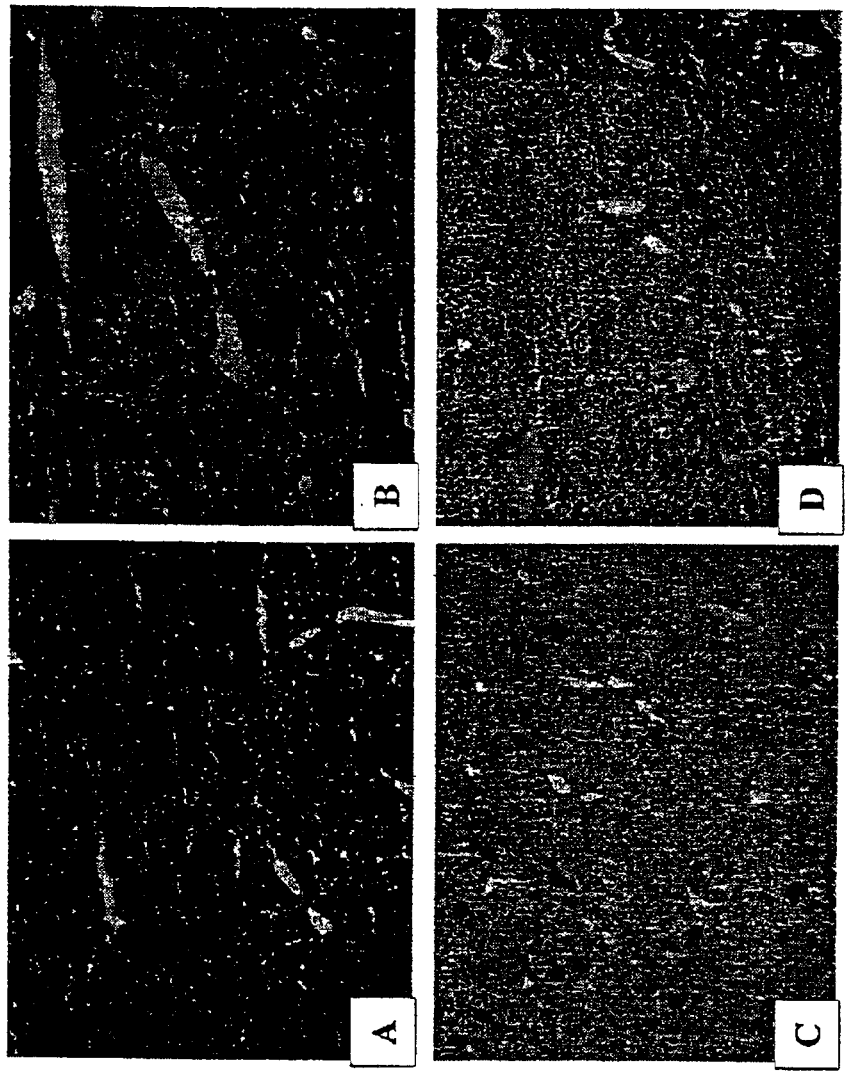

FIG. 6A demonstrates in situ X-gal staining of [E1–,E3–, 100K–] AdLacZ transduced murine liver. Liver samples were obtained from mice intravenously injected with the [E1–,E3–,100K–]AdLacZ vector and processed for in situ X-gal staining. Representative samples from each time point are presented. Magnification=100×. (A=3 days post-injection (dpi), B=28 dpi, C=56 dpi, D=84 dpi).

Figure 6B:
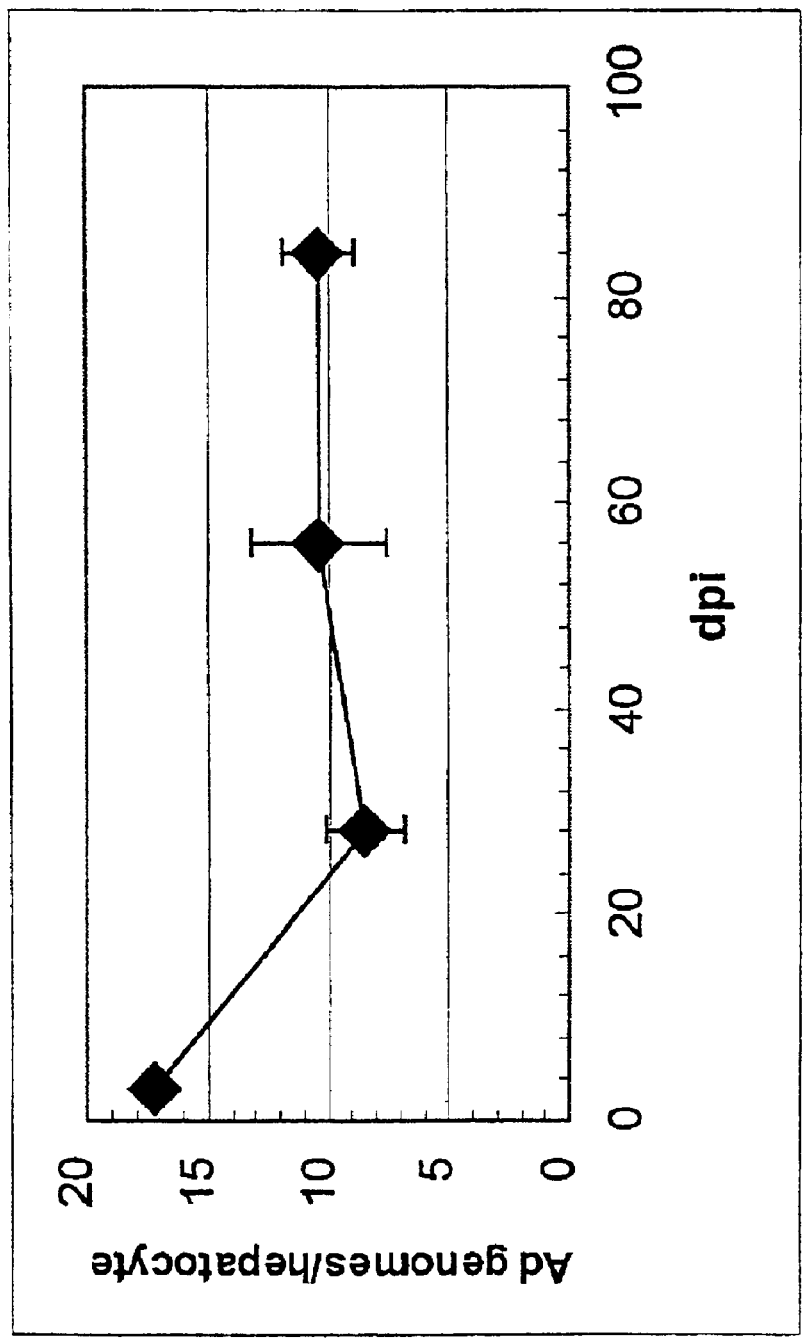

FIG. 6B demonstrates persistence of [E1–,E3–,100K–] AdLacZ vector genome DNA. Total DNA was extracted from the livers of [E1–,E3–, 100K–] AdLacZ infected mice at the indicated time points, and Ad vector genome copy numbers were determined by a non-competitive quantitative, Ad specific PCR. All values were normalized to G3PDH copy number standards. The amounts of vector DNA present at 28, 56, or 84 days post-injection (dpi) were not significantly different (p>0.05). The n=1 at 3 dpi, n=3 at 28 dpi, and n=2 at 28 and 56 dpi.

Figure 7:
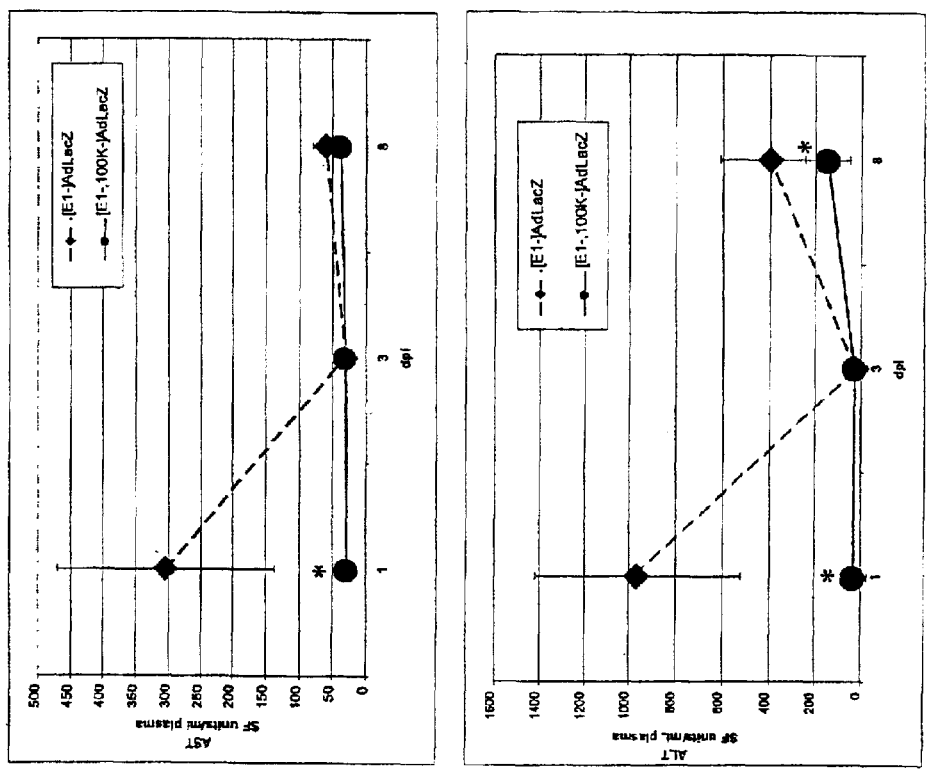

FIG. 7 shows a comparison of AST/ALT plasma levels after transduction of liver with [E1–,E3–]AdLacZ or [E1–, E3–,100K–]AdLacZ. $4\times10^9$ LacZ forming units of the respective vectors were intravenously injected into mice, and plasma samples were obtained from the animals at the indicated time points (n≧4 at 1 and 3 dpi, n=6 at 8 dpi). Similar levels of transduction were confirmed for both vectors after X-gal staining of liver samples derived from the animals (see FIG. 6A and data not shown). Those time points that demonstrated levels of AST or ALT that were significantly different (p<0.05 as determined by two-tailed Student T-test) between the indicated vectors are indicated by an "*".

DETAILED DESCRIPTION OF THE INVENTION

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

All publications, patent applications, patents, and other references mentioned herein are incorporated by reference in their entirety.

Except as otherwise indicated, standard methods may be used for the construction of the recombinant adenovirus genomes, helper adenoviruses, and packaging cells according to the present invention. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

The term "adenovirus" as used herein is intended to encompass all adenoviruses, including the Mastadenovirus and Aviadenovirus genera. To date, at least forty-seven human serotypes of adenoviruses have been identified (see, e.g., Fields et al., Virology, volume 2, chapter 67 (3d ed., Lippincoft-Raven Publishers). Preferably, the adenovirus is a serogroup C adenovirus, still more preferably the adenovirus is serotype 2 (Ad2) or serotype 5 (Ad5).

The various regions of the adenovirus genome have been mapped and are understood by those skilled in the art (see, e.g., FIELDS et al., VIROLOGY, volume 2, chapters 67 and 68 (3d ed., Lippincoft-Raven Publishers). The genomic sequences of the various Ad serotypes, as well as the nucleotide sequence of the particular coding regions of the Ad genome, are known in the art and may be accessed, e.g., from GenBank and NCBI (See, e.g., GenBank Accession Nos. J0917, M73260, X73487, AF108105, L19443, NC 003266 and NCBI Accession Nos. NC 001405, NC 001460, NC 002067, NC 00454).

Those skilled in the art will appreciate that the inventive adenovirus vectors may be modified or "targeted" as described in Douglas et al., (1996) Nature Biotechnology 14:1574; U.S. Pat. No. 5,922,315 to Roy et al.; U.S. Pat. No. 5,770,442 to Wickham et al.; and/or U.S. Pat. No. 5,712,136 to Wickham et al.

As used herein, the term "vector" or "gene delivery vector" may refer to an Ad particle that functions as a gene delivery vehicle, and which comprises vDNA (i.e., the vector genome) packaged within an Ad capsid. Alternatively, the term "vector" may be used to refer to the vector genome/vDNA when used as a gene delivery vehicle in the absence of the virion capsid.

An "Ad vector genome" refers to the viral genomic DNA, in either its naturally occurring or modified form. A "rAd vector genome" is a recombinant Ad genome (i.e., vDNA) that comprises one or more heterologous nucleotide sequence(s). The Ad vector genome or rAd vector genome will typically comprise the Ad terminal repeat sequences and packaging signal. An "Ad particle" or "rAd particle" comprises an Ad vector genome or rAd vector genome, respectively, packaged within an Ad capsid. Generally, the Ad vector genome is most stable at sizes of about 28 kb to 38 kb (approximately 75% to 105% of the native genome size). In the case of an adenovirus vector containing large deletions and a relatively small transgene, "stuffer DNA" can be used to maintain the total size of the vector within the desired range by methods known in the art.

A "heterologous nucleotide sequence" or "heterologous nucleic acid sequence" will typically be a sequence that is not naturally-occurring in the virus. Alternatively, a heterologous nucleotide or nucleic acid sequence may refer to a viral sequence that is placed into a non-naturally occurring environment (e.g., by association with a promoter with which it is not naturally associated in the virus).

As used herein, the term "polypeptide" encompasses both peptides and proteins, unless indicated otherwise.

By "infectious", as used herein, it is meant that the adenovirus can enter the cell by natural transduction mechanisms and express the transgene therein. Alternatively, an "infectious" adenovirus is one that can enter the cell by other mechanisms and express the transgene therein. As one illustrative example, the vector can enter a target cell by expressing a ligand or binding protein for a cell-surface receptor in the adenovirus capsid or by using an antibody (ies) directed against molecules on the cell-surface followed by internalization of the complex, as is described hereinbelow.

The term "replication" or "Ad replication" as used herein, refers specifically to replication of the Ad genome (i.e., making new copies of the virion DNA).

The term "propagation" as used herein refers to a productive viral infection wherein the viral genome is replicated and packaged to produce new virions, which typically can "spread" by infection of cells beyond the initially infected cell. A "propagation-defective" virus is impaired in its ability to produce a productive viral infection and spread beyond the initially infected cell.

Adeno-associated viruses (AAV) have also been employed as gene delivery vectors. AAV is a small, single-stranded DNA virus with a simple genomic organization. Two open reading frames encode a series of Rep and Cap polypeptides. Rep polypeptides (Rep50, Rep52, Rep68 and Rep78) are involved in replication, rescue and integration of the MV genome, although significant activity may be observed in the absence of all four Rep polypeptides. The Cap proteins (VP1, VP2, VP3) form the virion capsid. Flanking the rep and cap open reading frames at the 5' and 3' ends of the genome are 145 basepair inverted terminal repeats (ITRs), the first 125 basepairs of which are capable of forming Y- or T-shaped duplex structures. It has been shown that the ITRs represent the minimal cis sequences required for replication, rescue, packaging and integration of the AAV genome. Typically, in recombinant AAV vectors, the entire rep and cap coding regions are excised and replaced with a transgene of interest.

I. Replicating [100K−] Ad Vectors

Beyond the benefits afforded by the physical deletion of the 100K gene (e.g., increased carrying capacity and a decreased propensity to revert to a wild-type Ad during serial propagation), the investigations described herein demonstrate that 100K deleted Ad vectors are capable of replicating their genomes to high levels in the presence of the E1 genes. However, in the absence of 100K transcomplementation (e.g., demonstrated after [E1−, E3−, 100K−]AdLacZ infection of 293 cells) the amount of several of the late proteins that normally accumulates after Ad replication occurs may be diminished, and infectious virus production may be reduced or even eliminated. The studies presented herein further demonstrate that [100K−]Ad vectors may produce diminished levels of hepatotoxicity in vivo, suggesting that Ad late gene expression contributes to acute Ad vector hepatotoxicity.

First-generation (i.e., E1 defective) vectors are defective for replication in host cells unless the E1 gene products are provided in trans. In contrast, the inventive [E1+,100K−] vectors are replication-competent, and will amplify the Ad genome including the transgene, but the toxicity of the vector may be diminished due to the blockade of late gene expression as a result of loss of 100K activity. Moreover, the amount of transgene expression derived from the infected cells may be amplified, relative to similar infections with non-replicating Ad vectors. [E1+, 100K−]Ad mediated delivery of genes may further be used to enhance vaccination strategies, e.g., by providing high level expression within dendritic cells. Similarly, high level production of proteins encoded by the inventive Ad vectors may also be enhanced by replication of an [E1+,100K−] vector in producer cells, without the concomitant toxicity or production of infectious virus that is normally associated with Ad late gene expression.

Cells that have potentially limiting amounts of the coxsackie-adenovirus receptor [CAR] might also be targeted by replicating [E1+,100K−]Ad vectors. For example, muscle cells from adult mice appear to be more resistant to Ad vector infection, relative to muscle fibers in younger mice, apparently due to lower levels of CAR receptor expression in older mouse muscle fibers. Use of an [E1+, 100K−]Ad vector may enable high level Ad encoded transgene expression in those cells that are capable of being physically transduced by the vector, as opposed to similar infections with a non-replicating (e.g., E1−) Ad vector. For example, in those clinical situations where use of muscle as a platform for secretion of proteins is envisioned, improved expression and secretion from a limiting number of infected muscle fibers may allow for improved clinical efficacy as compared with a non-replicating vector. This embodiment may be used to express any polypeptide or RNA of interest, in particular, enzymes, more particularly, enzymes associated with a lysosomal storage disease or a glycogen storage disease, more particularly lysosomal acid α-glucosidase (GAA).

Further, strategies for cancer therapy may also benefit from the use of the inventive replicating 100K− vectors. For example, the amplified expression of a transgene encoding a cytotoxic polypeptide or RNA may enhance therapeutic efficacy as compared with a non-replicating vector containing the same transgene. This may allow one to use a lower viral dose to achieve a similar therapeutic effect. Alternatively, the 100K− vector may be used in conjunction with cancer immunotherapy approaches, e.g., to provide high level expression of a desired cancer cell antigen or other immunogen that induces an immune response against cancer cells.

The adenovirus vectors of the invention typically have E1 activity (i.e., produce functional E1a and E1b [e.g., p55] gene products sufficient for viral replication), but have an impairment in 100K protein activity (e.g., produce reduced levels of functional 100K protein). Those skilled in the art will appreciate that the term "sufficient for viral replication" is not intended to indicate that no other activities are necessary for replication. Rather, it is intended to signify that the activity of the specified protein(s) or gene product(s) is high enough to promote replication, such that, in the presence of any other required factors, replication will proceed.

The E1 genes may be transferred to a different region of the [100K−]Ad vector genome (e.g., optionally, a transgene of interest may then be inserted into the genome in place of the E1 coding region). This placement should not disrupt other vital Ad genes functions, especially those required for replication. In one particular embodiment, the E1 gene expression cassette is inserted into the 100K gene region.

The E1 (E1a and/or E1b) coding sequences may be operatively associated with an expression control sequence (e.g., a promoter) as known in the art. Promoters and other expression control sequences may be regulatable (e.g., inducible or tissue-specific) or constitutive. The expression control sequence or promoter may also be cancer cell specific. Expression control sequences and promoters are described in more detail hereinbelow in Section III. Regulated expression of the E1a and/or E1b genes may facilitate control over replication of the inventive vectors.

The Ad vectors of the invention have "an impairment in 100K activity" such that that the Ad vectors express a reduced level of functional 100K activity (alternatively, 100K transcripts or protein), e.g., less than about 50%, 25%, 20%, 15%, 10%, 5%, 2%, 1% or less as compared with a wild-type Ad or otherwise [100K+]Ad vector. Methods of assessing 100K activity are known by those skilled in the art (see, e.g., the Examples). As will be appreciated by those skilled in the art, 100K activity may be indirectly assessed by measuring 100K protein or mRNA transcript levels.

In embodiments of the invention, the Ad vector produces essentially no detectable 100K activity (alternatively, essentially no detectable 100K transcript or protein).

The [E1+, 100K−] Ad of the invention are replication competent, but impaired in their ability to propagate (as defined above), i.e., they are impaired in their ability to package new virions in the absence of transcomplementation of the defect in the 100K locus, for example, by a packaging cell that expresses the Ad 100K protein. As the adenovirus vectors of the invention are replication competent, they will typically express functional polymerase and preterminal proteins (i.e., are pol+ and pTP+). In embodiments of the invention, no new virions are detected following infection with the inventive [E1+, 100K−] Ad. Alternatively, production of new virions in infected cells may be reduced by at least about 50%, 60%, 70%, 80%, 90%, 95%, 98%, 99% or more as compared with a wild-type Ad infection or, alternatively, as compared with new virion production in a cell line that can transcomplement the loss of 100K function.

The Ad genome may be modified by any mutation known in the art (e.g., an insertion, missense, nonsense and/or deletion mutation) so as to result in an impairment in 100K activity expressed by the Ad genome. Preferably, the mutation or alteration to the 100K coding region is a deletion mutation, more preferably a deletion mutation that essentially ablates (e.g., essentially eliminates) 100K activity.

A mutation in the 100K coding region according to the present invention will typically not be a temperature-sensitive mutation.

The [100K−] vectors of the invention specifically exclude "gutted" adenovirus vectors (as that term is understood in the art, see e.g., Lieber, et al., (1996) *J. Virol.* 70:8944–60) in which essentially all of the adenovirus genomic sequences are deleted.

Thus, in preferred embodiments, the [E1+, 100K−]Ad has one or more deletions in the 100K coding region. The deletion(s) in the 100K coding region of the adenovirus genome preferably prevents, or essentially prevents, the expression of the 100K protein from the deleted region.

As used herein, a "functional" protein is one that retains at least one biological activity normally associated with that protein. Preferably, a "functional" protein retains all of the activities possessed by the unmodified protein. A "non-functional" protein is one that exhibits essentially no detectable biological activity normally associated with the protein (e.g., at most, only an insignificant amount).

The term "expresses essentially no functional 100K protein," as used herein, means that essentially no 100K protein and/or 100K activity is detectable (e.g., at most, only an insignificant amount is detectable) following infection of non-complementing cells with the inventive [E1+, 100K−] Ad vectors. The defect may be at the level of transcription, translation and/or post-translational processes. Thus, even if there is transcription and translation of the 100K gene, the resulting protein has essentially no detectable biological activity. 100K activity may be evaluated by any method known in the art.

The term "functional E1 coding region" is intended to indicate that Ad genome produces active forms of the E1a and E1b (e.g., p55) gene products sufficient for viral replication in the presence of all other required factors. As discussed hereinabove, the adenovirus genome may be engineered so that the functional E1 coding sequences are transferred to another location. Methods of measuring E1a and/or E1b coding region activity will be apparent to those skilled in the art, including indirect methods based on measurement of mRNA and protein or methods that evaluate new virion production or induction of CPE in target cells.

Likewise, the terms "functional E1a coding region" and "functional E1b coding region" are intended to indicate that the adenovirus genome produces an active form of the E1a or E1b (e.g., p55) gene products, respectively, sufficient for viral replication in the presence of all other required factors.

The term "deleted" as used herein refers to the omission of at least one nucleotide from the relevant coding region of the adenovirus genome. Deletions can be greater than about 1, 2, 3, 5, 7, 10, 15, 20, 50, 75, 100, 150, 200, or even 500 nucleotides, or more. Deletions in the relevant coding region of the adenovirus genome may be about at least 1%, 5%, 10%, 25%, 50%, 75%, 85%, 90%, 95%, 99%, or more of the coding region. Alternately, the entire coding region of interest (e.g., the entire 100K coding region) of the adenovirus genome is deleted. Preferably, the deletion will prevent or essentially prevent the expression of a functional protein from the coding region.

Preferably, the deletion in the 100K region encompasses nucleotides 24,990 to 25,687 of the adenovirus serotype 5 genome. Those skilled in the art will appreciate that similar deletions can be made in the homologous regions of the adenovirus genomes from other serotypes.

In general, larger deletions are preferred as these have the additional advantage that they will increase the carrying capacity of the deleted adenovirus for a heterologous nucleotide sequence of interest.

In particular embodiments, [E1+,100K-] Ad of the invention contain mutations or deletions in other regions of the adenovirus genome. Additional deletions may advantageously increase the carrying capacity of the vector and reduce the likelihood of recombination to generate replication competent virus. Preferably, the additional deletions do not unduly impair the ability of the resulting virus to replicate in desired target cells (e.g., does not reduce replication by more than about 40%, 50%, 60%, 70% or more). For example, the E3 coding region may be deleted without need for complementation.

Preferably, the deletion(s) in the adenovirus genome are selected so as not to interfere with other adenovirus functions essential for viral replication in target cells of interest. Likewise, the inventive adenovirus vectors generally express functional polymerase and preterminal protein activities.

In one particular embodiment, the inventive adenovirus vectors contain a mutation in the E1b region (i.e., is [E1b-]), such that the virus has an impairment in p55 protein activity. By "an impairment in E1b activity" it is meant that the adenovirus vectors express a reduced level of functional E1b activity e.g., less than about 50%, 25%, 20%, 15%, 10%, 5%, 2%, 1% or less, as compared with a wild-type or otherwise [E1b+] Ad vector. Methods of assessing E1b activity are known by those skilled in the art (see, e.g., the Examples). As will be appreciated by those skilled in the art, E1b activity may be indirectly assessed by measuring p55 protein or mRNA transcript levels.

The term "expresses essentially no functional E1b activity," as used herein, means that essentially no E1b activity is detectable (e.g., at most, only an insignificant amount is detectable) following infection of non-complementing cells with the inventive [E1a+, E1b-, 100K-] Ad vectors.

The [E1a+, E1b-, 100K-] Ad will replicate preferentially in p53- (i.e., cancerous) cells as compared with p53+ (typically, non-cancerous) cells. Adenovirus mutations that result in impairment in E1b activity are known in the art (see e.g., Steinwaerder et al., (2001) *Nature Med.* 7:240; Bischoff et al., (1996) *Science* 274:373); U.S. Pat. No. 6,080,578; U.S. Pat. No. 5,846,945).

As described in more detail hereinbelow, the inventive adenoviruses may additionally contain one or more heterologous nucleotide sequences (e.g., two, three, four, five, six or more sequences) of interest.

The inventive deleted adenoviruses are impaired in their ability to propagate (i.e., produce new virions) without complementation to compensate for the loss of 100K function, e.g., by a packaging cell. As described in more detail hereinbelow, the packaging cell will typically be stably modified (e.g., by chromosomal integration or episomal expression) to express a functional 100K protein. In the presence of transcomplementing functions, the [E1+, 100K-] Ad vectors of the invention can replicate and package new virions.

The inventive adenovirus vectors may be provided as vector DNA or as a packaged adenovirus particle.

II. Reagents and Methods for Producing [E1+,100K-] Adenovirus

The inventive deleted adenovirus vectors may be generated as described herein or by any other method known in the art. For example, deleted adenoviruses can be generated by co-transfection of a shuttle plasmid containing a deletion(s) of interest (and optionally a heterologous nucleotide sequence) and either a plasmid encoding the remaining sequences of the adenovirus, or with virion DNA from a viable adenovirus, into an appropriate packaging cell. Co-transfection of the two molecules into the packaging cell followed by a successful recombination event between the two molecules (the shuttle plasmid also contains regions of homology to the adenovirus genome) results in the generation of the full-length vector genome, containing the deletion of interest and capable of propagation in the appropriate transcomplementing cell.

According to one particular method, the E1 coding region may be ligated into an adenovirus shuttle plasmid (e.g., pShuttle), e.g., by placing the E1 gene under control of the native E1 enhancer/promoter element. Alternatively, the E1 genes can be placed under the control of a heterologous enhancer or promoter element. According to this embodiment, the E1 genes may be transferred to a different region of the [100K-]Ad vector genome. This placement should not disrupt other vital adenovirus genes functions, especially those required for replication. In one particular embodiment, the E1 gene expression cassette is inserted into the 100K gene region.

Any foreign DNA sequence of interest may be inserted 3' to the E1 gene sequences. The final E1+ shuttle plasmid (preferably, encoding a transgene) may be recombined with a plasmid encoding an adenovirus genome containing the desired mutation (e.g., deletion) within the 100K coding region (e.g., the pAdEΔ100K- plasmid, see Examples) to produce a full length [E1+, 100K-] Ad vector genome within a plasmid. The resulting plasmid may be digested with an appropriate restriction enzyme(s) to release the linear [E1+, 100K-] Ad vector genome. The [E1+, 100K-] Ad vector genome may be transfected into a transcomplementing cell line.

Once the vector genome replicates and enters the late phase of the adenovirus life cycle, the transcomplementing cell line will permit the vector to complete growth and packaging by supplying the 100K activity not encoded by the vector. The resulting packaged vector may be amplified and purified, optionally to clinical grades, using techniques known in the art for adenovirus vectors (e.g., column chromatography).

In particular embodiments, the complementing cell line stably expresses (e.g., has stably incorporated into its genome or expresses from a stable episome, such as an Epstein Barr Virus episome) a 100K coding sequence. The packaging cell is preferably an animal cell (e.g., insect, avian, mammalian), more preferably, a mammalian cell. Expression of the 100K coding sequence may be inducible or constitutive, as known in the art. In more preferred embodiments, the cell line is the K-16 cell line or the C7 cell line constitutively expressing the adenovirus 100K protein (see Examples herein and WO 00/12740).

According to the inventive packaging methods described herein, the collected adenovirus preferably has a titer of at least 100 particles per cell, at least 1000 particles per cell, at least 10,000 particles per cell.

III. Recombinant Adenovirus Vectors

As used herein, a "recombinant Ad vector" is an Ad vector that carries one or more heterologous nucleotide sequences (i.e., transgenes), e.g., two, three, four, five or more heterologous nucleotide sequences. The adenovirus vectors of the present invention are useful for the delivery of nucleic acids to cells in vitro, ex vivo, and in vivo. In particular, the inventive vectors can be advantageously employed to deliver or transfer nucleic acids to animal, more preferably mammalian, cells. Nucleic acids of interest include nucleic acids encoding polypeptides, preferably therapeutic (e.g., for medical or veterinary uses) or immunogenic (e.g., for vaccines) polypeptides.

Alternatively, in particular embodiments of the invention, the nucleic acid of interest may encode an antisense nucleic acid, a ribozyme, (e.g., as described in U.S. Pat. No. 5,877,022), RNAs that effect spliceosome-mediated trans-splicing (see, Puttaraju et al., (1999) Nature Biotech. 17:246; U.S. Pat. No. 6,013,487; U.S. Pat. No. 6,083,702), interfering RNAs (RNAi) that mediate gene silencing (see, Sharp et al., (2000) Science 287:2431) or other non-translated RNAs, such as "guide" RNAs (Gorman et al., (1998) Proc. Nat. Acad. Sci. USA 95:4929; U.S. Pat. No. 5,869,248), and the like.

As a further alternative, the adenovirus vectors can be used to infect a cell in culture to express a desired gene product, e.g., to produce a polypeptide of interest (for example, lysosomal acid α-glucosidase). Preferably, the polypeptide is secreted into the medium and can be purified therefrom using routine techniques known in the art. Signal peptide sequences that direct extracellular secretion of proteins are known in the art and nucleotide sequences encoding the same can be operably linked to the nucleotide sequence encoding the polypeptide of interest by routine techniques known in the art. Alternatively, the cells can be lysed and the expressed recombinant protein can be purified from the cell lysate. The cell may be a bacterial, protozoan, plant, yeast, fungus, or animal cell. Preferably, the cell is an animal cell (e.g., insect, avian or mammalian), more preferably a mammalian cell. Also preferred are cells that are permissive for transduction by adenoviruses.

The inventive methods may be used to express any polypeptide of interest, e.g., a therapeutic polypeptide, as described below. Alternatively, the polypeptide may be for use in an industrial process, in particular, an industrial enzyme. Industrial enzymes are known in the art and include, but are not limited to, cellulases, lipases, β-glucanases, hemicellulases, alkaline proteases, α-amylases, xylanases, catalases, lactases, pectinases, isoamylases, amyloglucosidases, invertases, phytases, rennet, and tannases.

Heterologous nucleotide sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

The present invention also provides vectors useful as vaccines. The antigen can be presented in the adenovirus capsid, alternatively, the antigen can be expressed from a heterologous nucleic acid introduced into a recombinant adenovirus genome and carried by the inventive adenoviruses. Any immunogen of interest can be provided by the adenovirus vector. Immunogens of interest are well-known in the art and include, but are not limited to, immunogens from human immunodeficiency virus (e.g., envelope proteins), influenza virus, gag proteins, cancer antigens, HBV surface antigen and cytomegalovirus pp65 (each to immunize against hepatitis), rabies glycoproteins, and the like.

An immunogenic polypeptide, or immunogen, may be any polypeptide suitable for protecting the subject against a pathogenic disease, including but not limited to bacterial, protozoal, fungal, and viral diseases. For example, the immunogen may be an orthomyxovirus immunogen (e.g., an influenza virus immunogen, such as the influenza virus hemagglutinin (HA) surface protein or the influenza virus nucleoprotein gene, or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogen may also be an arenavirus immunogen (e.g., Lassa fever virus immunogen, such as the Lassa fever virus nucleocapsid protein gene and the Lassa fever envelope glycoprotein gene), a poxvirus immunogen (e.g., vaccinia, such as the vaccinia L1 or L8 genes), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP genes), a bunyavirus immunogen (e.g., RVFV, CCHF, and SFS viruses), or a coronavirus immunogen (e.g., an infectious human coronavirus immunogen, such as the human coronavirus envelope glycoprotein gene, or a porcine transmissible gastroenteritis virus immunogen, or an avian infectious bronchitis virus immunogen). The immunogen may further be a polio immunogen, herpes immunogen (e.g., CMV, EBV, HSV immunogens) mumps immunogen, measles immunogen, rubella immunogen, diptheria toxin or other diptheria immunogen, pertussis immunogen, hepatitis (e.g., hepatitis A or hepatitis B) immunogen, or any other vaccine immunogen known in the art.

Alternatively, the immunogen may be any cancer cell antigen (including tumor cell antigens), or any other antigen that induces an immune response against cancer cells. A "cancer cell antigen," as used herein, is an antigen that is associated cancer in general or with a particular cancer. Preferably, the cancer cell antigen is expressed on the surface of the cancer cell. Exemplary cancer cell antigens are described in S. A. Rosenberg, (1999) Immunity 10:281). Other illustrative cancer cell antigens include, but are not limited to: the BRCA1 gene product, BRCA2 gene product, gp100, tyrosinase, GAGE-1/2, BAGE, RAGE, NY-ESO-1, CDK-4, β-catenin, MUM-1, Caspase-8, KIAA0205, HPVE, SART-1, PRAME, p15, melanoma tumor antigens (Kawakami et al., (1994) Proc. Natl. Acad. Sci. USA 91:3515; Kawakami et al., (1994) J. Exp. Med., 180:347; Kawakami et al., (1994) Cancer Res. 54:3124), MART-1 (Coulie et al., (1991) J. Exp. Med. 180:35), gp100 (Wick et al., (1988) J. Cutan. Pathol. 4:201), MAGE antigen, MAGE-1, MAGE-2 and MAGE-3 (Van der Bruggen et al., (1991) Science, 254:1643), CEA, TRP-1, TRP-2, P-15, HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) Ann. Rev. Biochem. 62:623), mucin antigens (international patent publication WO 90/05142), telomerases; nuclear matrix proteins, prostatic acid phosphatase, papilloma virus antigens, and antigens associated with the following cancers: melanomas, metastases, adenocarcinoma, thymoma, lymphoma, sarcoma, lung cancer, liver cancer, colon cancer, non-Hodgkins lymphoma, Hodgkins lymphoma, leukemias, uterine cancer, breast cancer, prostate cancer, ovarian cancer, cervical cancer, bladder cancer, kidney cancer, pancreatic cancer and others (see, e.g., Rosenberg, (1996) *Ann. Rev. Med.* 47:481–91).

The present invention may be further used to deliver a therapeutic polypeptide. Therapeutic polypeptides include, but are not limited to, cystic fibrosis transmembrane regulator protein (CFTR), dystrophin (including the protein product of dystrophin mini-genes, see, e.g, Vincent et al., (1993) *Nature Genetics* 5:130), utrophin (Tinsley et al., (1996) *Nature* 384:349), clotting factors (e.g., Factor XIII, Factor IX, Factor X, etc.), erythropoietin, angiostatin, endostatin, catalase, tyrosine hydroxylase, superoxide dismutase, leptin, the LDL receptor, lipoprotein lipase, omithine transcarbamylase, β-globin, α-globin, spectrin, α-antitrypsin, adenosine deaminase, hypoxanthine guanine phosphoribosyl transferase, β-glucocerebrosidase, sphingomyelinase, lysosomal hexosaminidase, branched-chain keto acid dehydrogenase, cytokines (e.g., α-interferon, β-interferon, interferon-γ, interleukin-2, interleukin-4, granulocyte-macrophage colony stimulating factor, lymphotoxin, and the like), peptide growth factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, glial derived growth factor, transforming growth factor -α and -β, and the like), receptors (e.g., the tumor necrosis growth factor receptor), monoclonal antibodies (including single chain monoclonal antibodies). Other illustrative heterologous nucleotide sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), and any other polypeptide that has a therapeutic effect in a subject in need thereof.

In particular preferred embodiments of the invention, the heterologous nucleotide sequence encodes a polypeptide that is associated with a metabolic disorder. By "associated with a metabolic disorder", it is intended that the expressed polypeptide is one that is deficient or defective in a metabolic disorder, or is otherwise a causative agent in a metabolic disorder.

In other particular preferred embodiments, the polypeptide is a lysosomal polypeptide, more preferably a precursor polypeptide that retains the mannose-6-phosphate residues that are characteristic of proteins targeted to the lysosomal compartment.

In still further preferred embodiments, the heterologous nucleotide sequence encodes a polypeptide that is associated with a lysosomal storage disease. By "associated with a lysosomal storage disease", it is intended that the expressed polypeptide is one that is deficient or defective in a lysosomal storage disorder, or is otherwise a causative agent in a lysosomal storage disorder.

There are a multitude of lysosomal storage diseases, as is well-known in the art. Exemplary lysosomal storage disease include, but are not limited to, GM1 gangliosidosis, Tay-Sachs disease, GM2 gangliosidosis (AB variant), Sandhoff disease, Fabry disease, Gaucher disease, metachromatic leukodystrophy, Krabbe disease, Niemann-Pick disease (Types A-D), Farber disease, Wolman disease, Hurler Syndrome (MPS IH), Scheie Syndrome (MPS IS), Hurler-Scheie Syndrome (MPS IH/S), Hunter Syndrome (MPS II), Sanfilippo A Syndrome (MPS IIIA), Sanfilippo B Syndrome (MPS IIIB), Sanfilippo C Syndrome (MPS IIIC), Sanfilippo D Syndrome (MPS IIID), Morquio A disease (MPS IVA), Morquio B disease (MPS IV B), Maroteaux-Lamy disease (MPS VI), Sly Syndrome (MPS VII), α-mannosidosis, β-mannosidosis, fucosidosis, aspartylglucosaminuria, sialidosis (mucolipidosis I), galactosialidosis (Goldberg Syndrome), Schindler disease, mucolipidosis II (I-Cell disease), mucolipidosis III (pseudo-Hurler polydystrophy), cystinosis, Salla disease, infantile sialic acid storage disease, Batten disease (juvenile neuronal ceroid lipofuscinosis), infantile neuronal ceroid lipofuscinosis, mucolipidosis IV, and prosaposin.

Polypeptides that are associated with lysosomal storage diseases according to the present invention include, but are not limited to, β-galactosidase, β-hexosaminidase A, β-hexosaminidase B, $GM_2$ activator protein, glucocerebrosidase, arylsulfatase A, galactosylceramidase, acid sphingomyelinase, acid ceramidase, acid lipase, α-L-iduronidase, iduronate sulfatase, heparan N-sulfatase, α-N-acetylglucosaminidase acetyl-CoA, glucosaminide acetyltransferase, N-acetylglucosamine-6-sulfatase, arylsulfatase B, β-glucuronidase, α-mannosidase, β-mannosidase, α-L-fucosidase, N-aspartyl-β-glucosaminidase, α-neuraminidase, lysosomal protective protein, α-N-acetyl-galactosaminidase, N-acetylglucosamine-1-phosphotransferase, cystine transport protein, sialic acid transport protein, the CLN3 gene product, palmitoyl-protein thioesterase, saposin A, saposin B, saposin C, and saposin D.

The present invention further provides recombinant adenovirus vectors carrying a transgene encoding a polypeptide associated with a glycogen storage disease. By "associated with a glycogen storage disease", it is intended that the expressed polypeptide is one that is deficient or defective in a glycogen storage disease, or is otherwise a causative agent in a glycogen storage disease.

There are a multitude of glycogen storage diseases (GSD), as is well-known in the art. Exemplary glycogen storage diseases include, but are not limited to, Type Ia GSD (von Gierke disease), Type Ib GSD, Type Ic GSD, Type Id GSD, Type II GSD (including Pompe disease or infantile Type II GSD), Type IIIa GSD, Type IIIb GSD, Type IV GSD, Type V GSD (McArdle disease), Type VI GSD, Type VII GSD, glycogen synthase deficiency, hepatic glycogenosis with renal Fanconi syndrome, phosphoglucoisomerase deficiency, muscle phosphoglycerate kinase deficiency, phosphoglycerate mutase deficiency, and lactate dehydrogenase deficiency.

Polypeptides that are associated with glycogen storage diseases according to the present invention include, but are not limited to, glucose 6-phosphatase, lysosomal acid α glucosidase, glycogen debranching enzyme, branching enzyme, muscle phosphorylase, liver phosphorylase, phosphorylase kinase, muscle phosphofructokinase, glycogen synthase, phosphoglucoisomerase, muscle phosphoglycerate kinase, phosphoglycerate mutase, and lactate dehydrogenase.

In more preferred embodiments, the deleted recombinant adenovirus vector carries a transgene encoding a lysosomal acid α-glucosidase (GAA), e.g., to treat Type II GSD including infantile (Pompe disease), juvenile and adult onset forms of the disease. More preferably, the lysosomal acid α-glucosidase is a human lysosomal acid α-glucosidase (hGAA). The transgene may encode either the mature GAA protein (e.g., the 76 kD form) or a GAA precursor (e.g., the 110 kD form). Preferably, the transgene encodes a GAA precursor. The term "GAA" as used herein encompasses mature and precursor GAA proteins as well as modified (e.g., truncated or mutated) GAA proteins that retain biological function (i.e., have at least one biological activity of the native GAA protein, e.g., can hydrolyze glycogen).

Lysosomal acid α-glucosidase (E.C. 3.2.1.20) (1,4-α-D-glucan glucohydrolase), is an exo-1,4-α-D-glucosidase that hydrolyses both α-1,4 and α-1,6 linkages of oligosaccharides liberating glucose. It catalyzes the complete degradation of glycogen with slowing at branching points. The 28 kb acid α-glucosidase gene on chromosome 17 encodes a 3.6 kb mRNA which produces a 951 amino acid polypeptide (Hoefsloot et al., (1988) *EMBO J.* 7:1697; Martiniuk et al., (1990) *DNA and Cell Biology* 9:85). The nucleotide sequence of a cDNA coding for the polypeptide, as well as the deduced amino acid sequence is provided in Hoefsloot et al. (Id.). The first 27 amino acids of the polypeptide are typical of a leader sequence of a signal peptide of lysosomal and secretory proteins. The enzyme receives co-translational N-linked glycosylation on the endoplasmic reticulum. It is synthesized as a 110-kDa precursor form, which matures by extensive modification of its glycosylation, and phosphorylation and by proteolytic processing through an approximately 90-kDa endosomal intermediate into the final lysosomal 76 and 67 kDa forms (Hoefsloot, (1988) *EMBO J.* 7:1697; Hoefsloot et al., (1990) *Biochem. J.* 272:485; Wisselaar et al., (1993) *J. Biol. Chem.* 268:2223; Hermans et al., (1993) *Biochem. J.* 289:681).

The human GAA gene as described by Hoefsloot et al., (1988) *EMBO J.* 7:1697 and Van Hove et al., (1996) *Proc. Natl. Acad. Sci. USA* 93:65, includes 5' untranslated sequences. In particular preferred embodiments, the hGAA transgene includes the entire approximately 3.8 kb sequence described by Van Hove et al. Alternatively, the deleted adenoviruses of the present invention may encode more or less of the 5' and 3' untranslated regions of the GAA gene.

Those skilled in the art will appreciate that the heterologous nucleotide sequence(s) are preferably operably associated with the appropriate expression control sequences. For example, the recombinant adenovirus vectors of the invention preferably contain appropriate transcription/translation control signals and polyadenylation signals operably associated with the heterologous nucleic acid sequence(s) to be delivered to the target cell. Those skilled in the art will appreciate that a variety of promoter/enhancer elements may be used depending on the level and tissue-specific expression desired. The promoter can be constitutive or inducible (e.g., the metallothionine promoter or a hormone inducible promoter), depending on the pattern of expression desired. The promoter may be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest. Brain-specific, hepatic-specific (e.g., alpha-1 antitrypsin promoter), prostate-specific, and muscle-specific (including skeletal, cardiac, smooth, and/or diaphragm-specific) promoters are more preferred. Also preferred are cancer cell specific promoter. Mammalian promoters are also preferred.

The heterologous nucleotide sequence(s) may be operatively associated with a cytomegalovirus (CMV) major immediate-early promoter, an albumin promoter, an Elongation Factor 1-α (EF1-α) promoter, a PγK promoter, a MFG promoter, or a Rous sarcoma virus promoter. It has been speculated that driving heterologous nucleotide transcription with the CMV promoter results in down-regulation of expression in immunocompetent animals (see, e.g., Guo et al., (1996) *Gene Therapy* 3:802). Accordingly, it is also preferred to operably associate the heterologous nucleotide sequence(s) with a modified CMV promoter that does not result in this down-regulation of transgene expression.

In embodiments wherein there is more than one heterologous nucleotide sequence, those skilled in the art will appreciate that the heterologous nucleotide sequences may be operatively associated with a single upstream promoter and one or more downstream internal ribosome entry site (IRES) sequences (e.g., the picornavirus EMC IRES sequence).

In embodiments of the invention in which the heterologous nucleotide sequence(s) will be transcribed and then translated in the target cells, specific initiation signals are generally required for efficient translation of inserted protein coding sequences. These exogenous translational control sequences, which may include the ATG initiation codon and adjacent sequences, can be of a variety of origins, both natural and synthetic.

IV. Gene Transfer Technology

The methods of the present invention provide a means for delivering heterologous nucleotide sequences into a broad range of host cells, including both dividing and non-dividing cells in vitro or in vivo. The vectors, methods and pharmaceutical formulations of the present invention are additionally useful in a method of administering a polypeptide to a subject in need thereof, as a method of treatment or otherwise. In this manner, the polypeptide may thus be produced in vivo in the subject. The subject may be in need of the polypeptide because the subject has a deficiency of the polypeptide, or because the production of the polypeptide in the subject may impart some therapeutic effect, as a method of treatment or otherwise, and as explained further below.

In general, the present invention can be employed to deliver any foreign nucleotide sequence to treat or ameliorate the symptoms associated with any disorder related to gene expression. Illustrative disease states include: lysosomal storage diseases, glycogen storage diseases, hemophilias (e.g., hemophilia A and hemophilia B) and other clotting disorders, Gaucher's Disease, diabetes mellitus, cystic fibrosis (and other diseases of the lung), muscular dystrophies (e.g., Duchenne, Becker), diseases of the nervous system (e.g., Alzheimer's Disease, Parkinson's Disease, amyotrophic lateral sclerosis, epilepsy), retinal degenerative diseases (and other diseases of the eye), diseases of solid organs (e.g., brain, liver, kidney, heart), and any other diseases having an infectious or genetic basis.

Alternatively, a gene transfer vector may be administered that encodes any therapeutic polypeptide.

Gene transfer has substantial potential use in understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus the methods of the present invention permit the treatment of genetic diseases. As used herein, a disease state is treated by partially or wholly remedying the deficiency or imbalance that causes the disease or makes it more severe. The use of site-specific recombination of nucleic sequences to cause mutations or to correct defects is also possible.

The instant invention can also be employed to provide an antisense nucleic acid to a cell in vitro or in vivo. Expression of the antisense nucleic acid in the target cell diminishes expression of a particular protein by the cell. Accordingly, antisense nucleic acids can be administered to decrease expression of a particular protein in a subject in need thereof. Antisense nucleic acids can also be administered to cells in vitro to regulate cell physiology, e.g., to optimize cell or tissue culture systems. The present invention is also useful to deliver other non-translated RNAs, e.g., ribozymes or "guide" RNAs (see, e.g., Gorman et al., (1998) *Proc. Nat. Acad. Sci. USA* 95:4929) to a target cell.

Finally, the instant invention finds further use in diagnostic and screening methods, whereby a gene of interest is transiently or stably expressed in a cell culture system.

V. Immunization Methods

As a further aspect, the present invention provides a method of producing an immune response in a subject, comprising administering an Ad vector carrying a nucleotide sequence encoding an immunogen to a subject, and an active immune response is mounted by the subject against the immunogen. Immunogens are as described hereinabove. Preferably, a protective immune response is elicited.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation, in* Immunology: Basic Processes 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment of disease, in particular cancer or tumors (e.g., by causing regression of a cancer or tumor and/or by preventing metastasis and/or by preventing growth of metastatic nodules). The protective effects may be complete or partial, as long as the benefits of the treatment outweigh any disadvantages thereof.

The Ad vector expressing the immunogen may be administered directly to the subject, as described below.

Alternatively, the Ad vector may be administered to a cell ex vivo and the altered cell is administered to the subject. The heterologous nucleotide sequence is permitted to be introduced into the cell, and the cell is administered to the subject, where the heterologous nucleotide sequence encoding the immunogen is preferably expressed and induces an immune response in the subject against the immunogen. Preferably, the cell is an antigen presenting cell (e.g., a dendritic cell) or a cancer.

According to the foregoing methods of inducing an immune response in a subject, it is preferred that the Ad vector carrying the heterologous nucleotide sequence is administered in an immunogenically effective amount, as described below.

As described in more detail below, the present invention also encompasses methods of treating cancer using immunotherapy by administration of Ad vectors expressing cancer cell antigens or any other immunogen that produces an immune response against a cancer cell. In one particular embodiment, an immune response may be produced against a cancer cell antigen in a subject by administering an Ad vector comprising a heterologous nucleotide sequence encoding the cancer cell antigen, for example to treat a patient with cancer. The Ad vector may be administered to a subject in vivo or by using ex vivo methods, as described herein.

VI. Methods of Treating Cancer

As used herein, the term "cancer" encompasses tumor-forming cancers. Likewise, the term "cancerous tissue" encompasses tumors. A "cancer cell antigen" encompasses tumor antigens.

In particular embodiments, the inventive Ad vectors are administered as part of a method of treating cancer by administering anti-cancer agents (e.g., cytokines) or a cancer cell antigen or other immunogen that produces an immune response against a cancer cell. The Ad vector may be administered to a cell in vitro or to a subject in vivo or by using ex vivo methods, as described herein and known in the art.

The term "cancer" has its understood meaning in the art, for example, an uncontrolled growth of tissue that has the potential to spread to distant sites of the body (i.e., metastasize). Exemplary cancers include, but are not limited to, leukemias, lymphomas, colon cancer, renal cancer, liver cancer, breast cancer, lung cancer, prostate cancer, ovarian cancer, melanoma, and the like. Preferred are methods of treating and preventing tumor-forming cancers.

The term "tumor" is also understood in the art, for example, as an abnormal mass of undifferentiated cells within a multicellular organism. Tumors can be malignant or benign. Preferably, the inventive methods disclosed herein are used to prevent and treat malignant tumors.

Cancer cell antigens according to the present invention have been described hereinabove. By the terms "treating cancer" or "treatment of cancer", it is intended that the severity of the cancer is reduced or the cancer is at least partially eliminated. Preferably, these terms indicate that metastasis of the cancer is reduced or at least partially eliminated. It is further preferred that these terms indicate that growth of metastatic nodules (e.g., after surgical removal of a primary tumor) is reduced or at least partially eliminated. By the terms "prevention of cancer" or "preventing cancer" it is intended that the inventive methods at least partially eliminate or reduce the incidence or onset of cancer. Alternatively stated, the present methods slow, control, decrease the likelihood or probability, or delay the onset of cancer in the subject.

In particular embodiments, cells may be removed from a subject with cancer and contacted with the Ad vectors of the invention. The modified cell is then administered to the subject, whereby an immune response against the cancer cell antigen is elicited. This method is particularly advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, in particular embodiments of the invention, immunomodulatory cytokines (preferably, CTL inductive cytokines) are administered to a subject in conjunction with the methods described herein for producing an immune response or providing immunotherapy.

Cytokines may be administered by any method known in the art. Exogenous cytokines may be administered to the subject, or alternatively, a nucleotide sequence encoding a cytokine may be delivered to the subject using a suitable vector, and the cytokine produced in vivo.

VII. Subjects, Pharmaceutical Formulations, Vaccine and Modes of Administration

The present invention finds use in veterinary and medical applications. Suitable subjects include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects are the most preferred. Human subjects include neonates, infants, juveniles, and adults.

In particular embodiments, the present invention provides a pharmaceutical composition comprising a virus vector of the invention in a pharmaceutically-acceptable carrier and, optionally, other medicinal agents, pharmaceutical agents, carriers, adjuvants, diluents, and the like. For injection, the carrier will typically be a liquid. For other methods of administration, the carrier may be either solid or liquid, such as sterile, pyrogen-free water or sterile pyrogen-free phosphate-buffered saline solution. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

In general, a "physiologically acceptable carrier" is one that is not toxic or unduly detrimental to cells. Exemplary physiologically acceptable carriers include sterile, pyrogen-free water and sterile, pyrogen-free, phosphate buffered saline. Physiologically-acceptable carriers include pharmaceutically-acceptable carriers.

By "pharmaceutically acceptable" it is meant a material that is not biologically or otherwise undesirable, i.e., the material may be administered to a subject along with the viral vector without causing any undesirable biological effects. Thus, such a pharmaceutical composition can be used, for example, in transfection of a cell ex vivo or in administering a virus vector directly to a subject.

One aspect of the present invention is a method of transferring a nucleotide sequence to a cell. In the case of virus particles, the virus particles may be added to the cells at the appropriate multiplicity of infection according to standard transduction methods appropriate for the particular target cells. Titers of virus to administer can vary, depending upon the target cell type and the particular virus vector, and can be determined by those of skill in the art without undue experimentation. Typically, at least about $10^3$ particles, at least about $10^5$ particles, at least about $10^7$ particles, at least about $10^9$ particles, or at least about $10^{11}$ particles are administered to the cell.

Alternatively, administration of an adenovirus vector of the present invention can be accomplished by any other means known in the art. For example, adenovirus vectors can be targeted to cells, including cells that are not normally competent for transduction by adenoviruses using antibodies, e.g., as described in U.S. Pat. No. 5,861,156 to George et al.; U.S. Pat. No., 5,521,291 to Curiel et al. Alternatively, adenoviruses can be targeted to cell-surface proteins (e.g., receptors) by expressing a binding protein or ligand on the surface of the adenovirus, e.g., as described by Douglas et al., (1996) *Nature Biotechnology* 14:1574; U.S. Pat. No. 5,770,442 to Wickham et al.; and U.S. Pat. No. 5,712,136 to Wickham et al. Further, poly-cation conjugated adenovirus particles (e.g., polylysine conjugated particles) may be employed as described by Wu et al., (1989) *J. Biol. Chem.* 264:16985, Fisher et al. (1994) *Biochem. J.* 299:49; and U.S. Pat. No. 4,871,982.

The adenovirus vector genome may be administered as a nucleic acid molecule (i.e., not packaged within the adenovirus capsid) by any other method known in the art. In addition, a plasmid or other nucleic acid molecule encoding the adenovirus vectors of the invention may be introduced into a cell in vitro, ex vivo, or in vivo. As one exemplary embodiment, liposomes may be employed to deliver the adenovirus vector genome or nucleic acid molecule encoding the same. For example, for in vitro and ex vivo applications, standard methods for transforming cells with nucleic acid molecules, such as electroporation, lipofection, or calcium phosphate precipitation may be employed. As a further alternative, the adenovirus vector genome may be encoded by a viral vector other than an adenovirus vector.

The cell to be administered the inventive virus vectors can be of any type, including but not limited to neuronal cells (including cells of the peripheral and central nervous systems), retinal cells, epithelial cells (including dermal, gut, respiratory, bladder and breast tissue epithelium), muscle cells (including cardiac, smooth muscle, skeletal muscle, and diaphragm muscle), pancreatic cells (including islet cells), hepatic cells (e.g., parenchyma), fibroblasts, endothelial cells, germ cells, lung cells (including bronchial cells and alveolar cells), prostate cells, stem cells, progenitor cells, dendritic cells, and the like. Alternatively, the cell is a cancer cell (including tumor cells). Moreover, the cells can be from any species of origin, as indicated above. Preferred are cells that are permissive for adenovirus infection.

The adenovirus vectors of the invention may be employed to produce polypeptides of interest by cells in vitro. The adenovirus comprises a heterologous nucleotide sequence(s) that may encode any polypeptide of interest, as described hereinabove. The nucleotide sequence preferably encodes a therapeutic polypeptide or an industrial protein (i.e., for use in an industrial process). In more preferred embodiments, the heterologous nucleotide sequence encodes a GAA, more preferably human GAA, which may be isolated from the cells using standard techniques and administered to subjects with GAA deficiency using enzyme replacement protocols (see, e.g., Van der Ploeg et al., (1991) *J. Clin. Invest.* 87:513).

In particular embodiments of the invention, the cell has been removed from a subject, the adenovirus vector is introduced therein, and the cells are then replaced back into the subject. Methods of removing cells from subjects for treatment ex vivo, followed by introduction back into the subject are known in the art (see, e.g., U.S. Pat. No. 5,399,346). As a further alternative, the cells that are manipulated and then introduced into the subject are provided from another subject or cell line.

A further aspect of the invention is a method of treating subjects in vivo with the inventive virus vectors. Administration of the adenovirus vectors of the present invention to a human subject or an animal in need thereof can be by any means known in the art for administering virus vectors. The subject may be a mammalian subject, more particularly a human subject. In other embodiments, the subject is a subject that has been diagnosed with a lysosomal storage disease or a glycogen storage disease. More preferred are subjects who have been diagnosed with GAA deficiency. Also preferred are subjects with cancer.

Dosages will depend upon the mode of administration, the disease or condition to be treated, the individual subject's condition, the particular virus vector, and the gene to be delivered, and can be determined in a routine manner. Typically, with respect to viral particles, at least about $10^3$, at least about $10^5$, at least about $10^7$, at least about $10^9$, or at least about $10^{11}$ particles are administered to the subject per treatment. Exemplary doses are virus titers of about $10^7$–$10^{14}$ particles, about $10^7$–$10^{13}$ particles, or about $10^8$–$10^{12}$ particles.

A "therapeutically-effective" amount as used herein is an amount that provides sufficient expression of the heterologous nucleotide sequence delivered by the vector to provide some improvement or benefit to the subject. Alternatively stated, a "therapeutically-effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

In particular embodiments of the invention, more than one administration (e.g., two, three, four, or more administrations) may be employed to achieve therapeutic levels of gene expression.

Immunogenic compositions of the present invention comprise an immunogenic amount of infectious virus vectors as disclosed herein in combination with a pharmaceutically-acceptable carrier. An "immunogenic amount" is an amount of the infectious virus vectors that is sufficient to evoke an immune response in the subject to which the immunogenic composition is administered. Typical doses of Ad particles include an amount of from about $10^3$–$10^{14}$ particles, about $10^7$–$10^{13}$ particles, about $10^8$–$10^{12}$ particles, or about $10^4$–$10^8$ particles, depending upon the age and species of the subject being treated, and the immunogen against which the immune response is desired. Other appropriate doses of the inventive virus vectors for producing a desired immune response may be routinely determined by those skilled in the art.

Exemplary modes of administration include oral, rectal, transmucosal, topical, transdermal, inhalation, parenteral, e.g., intravenous, subcutaneous, intradermal, intramuscular (i.e., administration to cardiac, skeletal, diaphragm and/or smooth muscle), and intraarticular administration, and the like, as well as direct tissue (e.g., muscle) or organ injection (e.g., into the liver, into the brain for delivery to the central nervous system), alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer the virus in a local rather than systemic manner, for example, in a depot or sustained-release formulation.

In particularly preferred embodiments of the invention, the nucleotide sequence of interest is delivered to the liver of the subject. Administration to the liver can be achieved by any method known in the art, including, but not limited to intravenous administration, intraportal administration, intrabiliary administration, intra-arterial administration, and direct injection into the liver parenchyma.

Intramuscular delivery to skeletal muscle is also preferred.

The adenovirus vectors disclosed herein may alternatively be administered to the lungs of a subject by any suitable means, but are preferably administered by administering an aerosol suspension of respirable particles comprised of the inventive adenovirus vectors, which the subject inhales. The respirable particles may be liquid or solid. Aerosols of liquid particles comprising the inventive adenovirus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the inventive virus vectors may likewise be produced with any solid particulate medicament aerosol generator, by techniques known in the pharmaceutical art.

In particular embodiments, an Ad vector encoding a polypeptide is introduced into target cells (e.g., liver cells or skeletal muscle cells) and the polypeptide is expressed therein, and optionally secreted into the circulatory system, where it is delivered to target tissues, preferably, in a therapeutic amount. Intramuscular delivery to skeletal muscle or delivery to the liver are preferred in the practice of this embodiment of the invention.

VIII. Use of the Inventive Adenoviruses for Producing AAV Vectors

In particular embodiments, the adenovirus vectors of the invention are used as helper viruses in methods of producing adeno-associated virus (AAV) vector stocks. Advantageously, the inventive adenovirus vectors may be defective for late gene expression as a result of the lack of functional 100K protein, thereby substantially reducing or eliminating the risk of contamination of AAV stocks by adenovirus particles and adenovirus late gene products.

The adenovirus vector preferably comprises the adenovirus sequences which provide helper functions essential for a productive AAV infection. In particular, the adenovirus helper functions for AAV infection are provided by the adenovirus early genes, more particularly, the E1a, E2a, E4orf6 and VA RNA adenovirus sequences.

Whereas the inventive adenoviruses of the invention typically express functional polymerase and pTP proteins, those skilled in the art will appreciate that the [E1+, 100K−] Ad of the invention may further be pol- or pTP- (alternatively, or additionally, they may be impaired in other functions) as long as a packaging cell or helper that provides these functions is used for producing the AAV stock.

Any suitable method may be used to produce AAV vector stocks using the inventive [E1+, 100K−] Ad helper viruses (see, e.g., U.S. Pat. No. 5,139,941; U.S. Pat. No. 5,858,775; U.S. Pat. No. 6,146,874). In one method, AAV stocks may be produced by co-transfection of a rep/cap vector encoding AAV packaging functions and the template encoding the AAV vDNA into human cells infected with the helper adenovirus (Samulski et al., (1989) *J. Virology* 63:3822).

In particular embodiments, the adenovirus helper virus is a "hybrid" virus that encodes AAV Rep and/or capsid proteins. Amplification of the [E1+, 100K−] Ad vector genome may advantageously provide higher level expression of the AAV Rep and/or capsid sequences as compared with a non-replicating Ad.

"Hybrid" Ad/AAV vectors and methods of producing AAV stocks using these reagents are known in the art (see, e.g., U.S. Pat. Nos. 5,589,377; and 5,871,982, 6,251,677; and 6,387,368). Preferably, the hybrid Ad of the invention expresses the AAV capsid proteins (i.e., VP1, VP2, and VP3). Alternatively, or additionally, the hybrid adenovirus may express one or more of AAV Rep proteins (i.e., Rep40, Rep52, Rep68 and/or Rep78). The AAV sequences may be operatively associated with a tissue-specific or inducible promoter (each as defined hereinabove. In particular, in embodiments of the invention, the AAV rep coding sequences are operatively associated with a tissue-specific or inducible promoter.

The AAV vector genome and the AAV capsid proteins may be derived from the same or different AAV serotypes. The various AAV serotypes are described hereinabove. In particular embodiments, the AAV capsid and vector genome are derived from AAV-6. In other particular embodiments, the AAV capsid is an AAV6 capsid and the AAV vector genome is derived from a different AAV serotype (e.g., AAV-1, AAV-2, AAV-3, or AAV-5).

Having now described the invention, the same will be illustrated with reference to certain examples, which are included herein for illustration purposes only, and which are not intended to be limiting of the invention.

EXAMPLE 1

Cell Lines

Production of E1 and 100K Expressing Cell Lines:

Ad5 derived DNA was used as a template for the PCR amplification of the 100K open reading frame (ORF) using an EcoRI tailed forward primer:

5'-CGGAATTCGATCATGGAGTCAGTCGAG-3' (SEQ ID NO:1)

and an XbaI tailed reverse primer:

5'-GCCTCTAGAGTCCCATCTACGGTTGGG-3' (SEQ ID NO:2)

100 ng of each primer were included in a reaction mixture containing 10 mM KCl, 10 mM(NH$_4$)$_2$SO$_4$, 20 mM Tris-Cl (pH=8.75), 2 mM MgSO$_4$, 0.1% Triton X-100, 0.1 mg/ml bovine serum albumin, 25 mM of each dNTP, 2.5 units of a high fidelity Taq polymerase (Stratagene, La Jolla, Calif.) and 100 ng of Ad5 genomic DNA. After denaturation for 3 minutes at 95° C., the reaction mixture was subjected to a limited number of PCR amplification cycles consisting of DNA denaturation at 95° C. for 30 seconds, primer annealing at 55° C. for 45 seconds, and Taq mediated extension at 72° C. for 1.5 minutes. This same PCR reaction was utilized to screen genomic DNA from G-418 resistant cells for the presence of 100K specific DNA sequences (see below). The PCR yielded the predicted ~2.3 kb 100K specific product, which was digested with EcoRI and XbaI, and directionally ligated into the XbaI and EcoRI sites within pcDNA3 (Invitrogen, Carlsbad, Calif.), generating pcDNA3/100K. In this manner, the 100K ORF was placed under the expressional control of a CMV enhancer/promoter element. Two micrograms of the pcDNA3/100K plasmid was linearized with Cla I restriction enzyme digestion, and transfected into 293 cells (E1+) by the calcium phosphate method. Transfected cells were placed into medium containing 800 micrograms/ml of G-418 and clonal isolates of G-418 resistant cells were serially expanded. The subclones were screened for the ability to transcomplement the growth of the temperature-sensitive (ts) Ad5 100K mutant, H5ts116 (kindly supplied by Dr. H. Ginsberg, (Columbia University, New York) at the non-permissive temperature of 39° C. Of approximately thirty-five G-418 resistant cell lines, one (referred to as K-16) was found to be consistently capable of effectively transcomplementing growth of H5ts116 at 39° C.

Construction of an [E1−,100K−]Ad Vector:

The pAdEasy-1 plasmid (He et al., (1998) *Proc. Nat. Acad. Sci. USA* 95:2509), was used as a template for the generation of 100K deletions within the Ad5 genome (Id.). Briefly, pAdEasy-1 was digested with BamHI, and the subfragment containing the right end of the Ad5 genome (Ad5 sequences 21696 to 35,995) was isolated and subcloned into BamHI digested pcDNA3, yielding pAdEΔBamHI. The latter was digested with NheI to release a 687 bp fragment within the 100K gene (Ad5 sequences 24999 to 25686), and self-ligated, to generate pAdEΔBamHI/Δ100K. The pAdEΔBamHI/Δ100K plasmid was then digested with BamHI, and ligated to the large BamHI subfragment of pAdEasy-1 generating pAdEΔ100K.

A 3.1 kb Sal I fragment encompassing the bacterial B-galactosidase (LacZ) gene (kindly provided by Dr. W. Koch, Duke University) was ligated into the Sal I site of pShuttleCMV, generating pShuttleCMVLacZ (He et al., (1998) *Proc. Nat Acad. Sci. USA* 95:2509). The LacZ encoding shuttle plasmid was linearized with PmeI, and co-electroporated with pAdEΔ100K into BJ5183 *E. coli*. In this manner, targeted recombination between the two plasmids generated the full length [E1−,E3−,100K−]AdLacZ vector genome within a bacterial plasmid. Similarly, the pShuttleCMVLacZ plasmid was co-electroporated with pAdEasy-1 to generate the [E1−,E3−]AdLacZ vector containing plasmid.

Ten micrograms of the respective plasmids were digested with PacI and transfected either into 293 cells (for generation of the [E1−,E3−]AdLacZ vector) or into K-16 cells (for generation of the [E1−,E3−,100K−]AdLacZ vector). Within one week of transfection, extensive cytopathic effects were visible in both cell lines, indicating widespread vector growth and amplification. The infected cells were harvested, freeze-thawed, and the vectors were amplified. After infection of sixty 150 mm tissue culture plates, the respective vectors were purified, twice banded on CsCl$_2$ gradients, and titered for LacZ transducing units, as previously described (Amalfitano et al., 1998) *J. Virology* 72:926).

EXAMPLE 2

Replication Assays

The indicated cell lines were infected at a multiplicity of infection (MOI) of 5 with the respective vectors, incubated for 2 or 20 hours at 37° C., and total DNA was harvested. Ten micrograms of each sample were digested with EcoRV, electrophoresed through a 0.7% agarose gel, and the vector DNA visualized after ethidium bromide staining.

EXAMPLE 3

One Step, Limited Burst Assay

Indicated cell lines were infected at the indicated MOI's with the respective vectors, and total virus yield was measured by X-gal staining of C-7 cells infected with serial dilutions of the vector containing lysates, as previously described (Amalfitano et al., 1998) *J. Virology* 72:926).

EXAMPLE 4

Protein Analysis of Ad Infected Cell Lines

Indicated cell lines were infected with each of the vectors at an MOI of 5. Twenty hours post infection, the medium was replaced with methionine-free medium supplemented with $^{35}$S-methionine at 90 micro-Curies/ml medium. The cells were harvested 3 hours later, rinsed in PBS, and lysed in 50 mM Tris-CI (pH=6.8), 4% SDS, 2% B-Mercaptoethanol. The protein content of the cell lysates was determined against a protein standard curve via the Bradford assay, and 75 μg of each cell extract was electrophoresed in a 6.0% SDS-polyacrylamide gel. The gel was Coomassie stained, and photographed. Duplicate gels were dried down and subjected to autoradiography, the respective proteins were identified based upon their characteristic molecular weights, and analyzed using the SCION image-analysis software package.

EXAMPLE 5

RNA Detection of 100K Sequences

Total cellular RNA was isolated, electrophoretically separated, and ethidium bromide stained to confirm equivalent loading of the samples. The RNA samples were transferred to a nylon membrane and probed with the 2.3 kb, 100K specific, $^{32}$P-labeled Ad subfragment derived from digestion of pcDNA3/100K with EcoRI and XbaI. The nylon membrane was exposed to autoradiography film and the image photographed.

EXAMPLE 6

Southern Blot Analysis

Twenty micrograms of total liver DNA from infected mice was digested with EcoRI, electrophoretically separated, and transferred to a nylon membrane. Liver DNA isolated from non-infected animals were spiked with an [E1−]AdLacZ virus genome as a positive control. The membrane was hybridized to a [α-$^{32}$P] dCTP-labeled DNA probe (the ~5300 bp BstXI subfragment of Ad5). The membrane was washed, exposed to autoradiography films, and photographed.

EXAMPLE 7

Non-competitive, Quantitative Ad Specific PCR

Four hundred ng of liver DNA derived from each of the [E1−,E3−, 100K−] AdLacZ infected mice was subjected to PCR with the following Ad specific primers:

```
5'-GGTAGCACCACTGCAGAGCTTC-3', and    (SEQ ID NO:3)

5'-GGTCACAAGGGCGTCTCCAAG-3'          (SEQ ID NO:4)
```

(generating a 348 bp product) in the buffer described above, under the following cycling conditions: 94° C. for 3 minutes, followed by 22 cycles of 94° C. for 30 seconds, annealing at 55° C. for 30 seconds, and extension at 72° C. for 1 minute. Equivalent amounts of liver DNA derived from mock-infected mice were similarly amplified after being spiked with increasing amounts of adenovirus DNA, to generate a standard curve. The amounts of Ad specific PCR product derived from amplification of the infected liver samples were then determined after comparison to the standard curve data. To further normalize the assay, and be sure that the amount of Ad specific PCR product generated were from equivalent amounts of template, identical amplifications of the experimental DNA samples were carried out utilizing primers specific for the glyceraldehyde-3-phosphate dehydrogenase (G3PDH) gene:

```
5'-ACCACAGTCCATCGGATCAC-3', and    (SEQ ID NO:5)

5'-TCCACCACCCTGTTGCTGTA-3',        (SEQ ID NO:6)
```

(generating a 452 bp product) for 16 cycles of amplification, and compared to the amounts of G3PDH specific amplification product derived from standard amounts of mock infected murine liver DNA. All Ad genome copy numbers were then normalized to G3PDH concentration. All PCR products were visualized by ethidium bromide staining of 1.5% agarose gels after electrophoretic separation, and quantitated with the freeware version of the SCION imaging software.

EXAMPLE 8

Animal Injections, X-gal Staining, AST, ALT Analysis

Adult (7–9 week old) C57Bl/6 mice (Jackson Laboratories, Bar Harbor, Me.) were intra-venously injected (retro-orbital) with either PBS (mock) or PBS containing 4×10$^9$ LacZ transducing units of each of the respective vectors. Animals were sacrificed and liver tissues were harvested for DNA analysis, or processed for X-gal substrate staining (indicating LacZ expression) as previously described (Hodges et al., (2000) *J. Gene Med.* 2:250). Serial plasma samples derived from the infected mice were analyzed for evidence of Ad vector induced hepatitis by monitoring AST and ALT levels using the respective transaminase kits, per the manufacturers guidelines (Sigma, St. Louis, Mo.). Statistical analysis were performed using Student's Test. All animal procedures were done in accordance with Duke University Institutional Animal Care and Use Committee guidelines.

EXAMPLE 9

Production of E1 and 100K Expressing Cell Lines

To investigate the impact that lack of 100K activities has on Ad vector biology, deletions within the 100K gene were engineered. To enable the isolation of these vectors to high quantity (and in a helper-virus independent fashion) cell lines that could transcomplement the growth of 100K deleted Ad were isolated. To accomplish this, human 293 cells (E1+) were transfected with a 100K expression plasmid (pcDNA3/100K). Cells that had successfully integrated the pcDNA3/100K plasmid were initially identified by their ability to grow in high concentrations of G-418. It was determined whether the G-418 resistant cell lines expressed adequate amounts of 100K by assessing their ability to transcomplement the growth of a 100K ts Ad mutant, at the non-permissive temperature of 39° C. Of several G-418 resistant clones, one (K-16) was found to consistently allow for evidence of growth of the ts mutant H5ts116 at the non-permissive temperature, based upon visualization of viral induced cytopathic effects noted in the cells after infection at 39° C. (FIG. 1A). DNA isolated from the K-16 cells was evaluated by a PCR specific for sequences residing within the pcDNA3/100K plasmid; K-16 derived DNA demonstrated the presence of the 100K specific sequences, in contrast to the lack of such sequences in the parental 293 cells (FIG. 1B). Furthermore, total RNA derived from the K-16 cells contained large amounts of 100K specific mRNA, as compared to the lack of such transcripts in 293 cells (FIG. 1C). Unfortunately, utilization of 100K specific monoclonal antibodies was not able to detect 100K specific peptide within protein extracts derived from K-16 cells (data not shown). At this time it cannot be discerned whether the lack of sensitivity was simply due to technical difficulties with the antibodies utilized, or due to low levels of 100K protein expression within the cell lines (see results below).

EXAMPLE 10

Production of [E1–,100K–] Deleted Ad Vectors in K-16 Cells

To facilitate the construction of 100K deleted Ad vectors, previously described method for [E1–, E3–]Ad vector production (He et al., (1998) Proc. Natl. Acad. Sci. USA 95:2509) was modified. Reconstruction of pAdEasy-1 was undertaken (see Example 1) so as to introduce an extensive deletion within the 100K gene. The new plasmid was referred to as pAdEΔ100K (FIG. 2A). Recombination between a shuttle plasmid (containing the right end of the Ad genome juxtaposed to a CMV-LacZ transgene cassette) with pAdEΔ100K allowed us to generate the full length [E1–, E3–,100K–]AdLacZ vector genome within a bacterial plasmid. PacI restriction enzyme digestion of the plasmid, followed by transfection into K-16 cells, resulted in a productive infection as evidenced by the rapid onset of widespread cytopathic effects, and subsequent high level amplification and purification by cesium chloride banding. Final concentrations of the purified [E1–,E3–,100K–] AdLacZ vector were similar to those achieved with growth of [E1–,E3–]Ad vectors in 293 cells (data not shown). The [E1–,E3–,100K–]AdLacZ vector derived from this stock was titered for LacZ transducing units, and utilized for all subsequent experiments described below.

Confirmation of genome integrity as well as the replication potential of [E1–,E3–,100K–]AdLacZ was compared with the [E1–, E3–]AdLacZ vector (FIG. 2B). The results demonstrated that the two vector genomes were identical except for the presence of the 100K deletion. The results also confirmed the stability of 100K deleted vector genomes though repeated cycles of replication and amplification. Finally, both vectors appeared to be capable of replicating their respective genomes to near identical levels in this experiment.

EXAMPLE 11

High Level Growth of 100K Deleted Vectors

Repeated, 30 hour one-step burst assays demonstrated that infections of 293 cells with the [E1–,E3–]AdLacZ vectors yielded amounts of vector similar to those obtained after infection of K-16 cells with the [E1–, E3–,100K–] AdLacZ vector (FIG. 3). Although these experiments demonstrated that there was a slight reduction in the absolute yields of the [E1–,E3–,100K–] AdCMVLacZ from K-16 cells as compared with the yield of the [E1–,E3–] AdLAcZ vector in 293 cells, in practice this did not significantly affect the ability to produce high titer stocks of the [E1–,100K–] AdLacZ vector. In contrast, yields of the 100K deleted vector were significantly reduced when identical infections of 293 cells were simultaneously attempted (FIG. 3). The results confirmed that high level growth of the 100K deleted vector was dependent upon the transcomplementation of 100K functions provided by the K-16 cell line. As an additional control, 293, C-7, or K-16 cells were simultaneously infected with an [E1–,E2b–]AdLacZ vector, the latter is only capable of being grown to high titers when transcomplemented for both E1 and E2b functions in C-7 cells (Amalfitano et al., (1998) J. Virology 72:926). The [E1–,E2b–]AdLacZ vector was blocked in growth after infection of 293 or K-16 cells (to a similar degree as for the [E1–,100K]AdLacZ vector grown in 293 or C-7 cells) and only grew to high levels when transcomplemented in C-7 cells.

EXAMPLE 12

Replication and Late Gene Expression of [E1–,E3–100K–]Ad Vectors 293 cells (E1+) or K-16 cells (E1+,100K+) were infected with the [E1–, E3–,100K–]AdLacZ vector, and vector replication evaluated (FIG. 4). Whereas both cell lines had barely detectable levels of input vector DNA two hours after infection, high levels of vector specific DNA sequences (superimposed upon the cellular DNA genomic smear) were readily detected in both cell lines 20 hours after infection. The results confirmed that Ad genomes deleted for 100K were fully capable of replicating in the presence of the Ad E1 proteins. The replication results also demonstrated that Ad genome replication may be effectively uncoupled from the production of infectious virus by deletion of 100K gene functions, since infection of 293 cells with the [E1–,E3–, 100K–] AdLacZ vector yielded low levels of virus (FIG. 3).

Proteins derived from K-16 cells or several non-complementing cell lines infected with the [E1–,E3–, 100K–]AdLacZ vector were next compared to identical infections with other classes of modified Ad vectors. Whereas infection of 293, C-7, or K-16 cells with the [E1–,E3–]AdLacZ vector resulted in detection of high levels of the hexon, 100K, penton, and fiber proteins 24 hours post-infection, identical infections with the [E1–,E3–, 100K–]AdLacZ vector resulted in a significant decrease in the absolute amounts of each of these proteins in 293 or C-7 cells, a defect that was normalized for all proteins except 100K, when the 100K deleted vector infected K-16 cells (FIG. 5A). Interestingly 100K protein was not detected by this method in any of the cell lines tested, suggesting that even though K-16 cells express low levels of 100K (relative to a wild-type infection) the low amounts actually expressed are adequate to transcomplement the hexon, penton, and fiber expression defect of the [E1–,E3–,100K–]AdLacZ vector. The results indirectly suggest that wild-type Ad may actually express excessive amounts of the 100K peptide, more than is required to assemble significant amounts of infectious virus.

The hexon, 100K, penton, and fiber protein level defects were also analyzed after radiolabeling of viral proteins during the late phase of vector infection of 293 or K-16 cells (FIG. 5B). These experiments demonstrated that there was at least a 65% decline (based upon quantitative image analysis; FIG. 5B) in the amount of hexon that was radiolabeled in 293 cells infected with the [E1–,E3–,100K–]AdLacZ vector, as compared with infection of 293 cells infected with identical amounts of the [E1–,E3–]AdLacZ vector. Importantly, K-16 cells infected with the [E1–,E3–,100K–] AdLacZ vector demonstrated a nearly normalized restoration of hexon radio-labeling. The results suggest that lack of hexon accumulation in 293 cells infected with the [E1–, E3–,100K–] AdLacZ vector was due to a lack of adequate synthesis of hexon, possibly related to the influence by the 100K protein on late mRNA translation rates (Adam et al., (1987) *J. Virology* 61:3276; Matthews, (1990) *Enzyme* 44:250; Riley et al., (1993) *J. Virology* 67:3586). The assay also confirmed an absence of 100K protein when the [E1−, E3−, 100K−]AdLacZ vector infected either 293 or K-16 cells. Despite lack of 100K detection, the latter results again confirmed that K-16 cells express adequate amounts of 100K, since these cells adequately transcomplemented the hexon expression defect of [E1−,E3−,100K−]AdLacZ.

In contrast to the patterns observed for hexon and 100K, there was no evidence of significant decreases of radiolabeled penton or fiber proteins after [E1−,E3−,100K−] AdLacZ infection of 293 cells (FIG. 5B). These observations suggest that a lack of stable accumulation of the penton and fiber proteins occurred in [E1−,E3−,100K−]AdLacZ infected 293 cells, (see FIG. 5A) rather than a direct effect of 100K upon the rates of expression/translation of penton or fiber per se.

The blockade to late gene expression exhibited by the [E1−,E3−, 100K−] AdLacZ in 293 cells was also qualitatively similar to that observed when a completely replication incompetent Ad vector ([E1−,E3−,E2b−] AdLacZ) was utilized to infect 293 cells (E1+,E2b−) cells (as determined by Coomassie staining of infected cell proteins: FIG. 5A). The [E1−,E3−,E2b−]AdLacZ vector was previously demonstrated to have a profound replication blockade after infection of 293 cells, a blockade that is also responsible for a significant blockade to late gene expression derived from these vectors (Amalfitano et al., (1998) *J. Virology* 72:926). The latter is due to the fact that cis-activation of the Ad major late promoter (MLP) and subsequent late gene expression derived from the MLP, are both dependent upon Ad genome replication (Thomas et al., (1980) *Cell* 22:523). The 100K vectors, however, retain the ability to replicate their genomes (in contrast to [E1−,E3−,E2b−] Ad vectors) when in the presence of high levels of E1 activity (FIG. 3; Amalfitano et al., (1998) *J. Virology* 72:926; Hodges et al., (2000) *J. Gene Med.* 2:250).

EXAMPLE 13
Analysis of Acute Liver Toxicity and in vivo Persistence of [E1−,E3−,100K−]AdLacZ In vivo studies were undertaken to evaluate whether the late gene expression blockade afforded by deletion of 100K reduces the acute hepatotoxicity of Ad vectors in vivo. It was first demonstrated that the [E1−, E3−, 100K−]AdLacZ vector could efficiently transduce hepatocytes in vivo, since >75% of the hepatocytes were demonstrated to express the LacZ gene 3 days after injection of $4 \times 10^9$ LacZ forming units of the vector (FIG. 6A). The level of transduction was identical to that noted after injection of similar amounts of the [E1−,E3−]AdLacZ vector (data not shown). In contrast to the [E1−,E3−,100K−]AdLacZ vector, however, injection of the [E1−,E3−,100K−] AdLacZ vector resulted in a significantly reduced amount of liver derived plasma ALT levels at both 1 and 8 days post-injection, with AST levels also significantly lower at 1 day post-injection (FIG. 7). The results demonstrated that deletion of 100K reduces the acute hepatotoxicity of Ad vectors that contain this deletion.

Analysis of the infected mice after prolonged periods of time was also carried out. For example, after intra-venous injection of the [E1−, E3−, 100K−] AdLacZ vector, the number of LacZ positive hepatocytes declined from 75–100% at 3 dpi, to <5% after 3 months (FIG. 6A, panels A–D). The lack of LacZ expression was not, however, due to lack of persistence of the [E1−,E3−,100K−]AdLacZ vector genome, since both Southern blot analysis (data not shown) and a quantitative adenovirus specific PCR assay demonstrated persistence of the vector for up to 12 weeks in all injected animals (FIG. 6B). It was concluded that lack of persistent LacZ expression in [E1−,E3−,100K−] AdLacZ infected hepatocytes was not due to the loss of vector DNA, but was rather due to CMV enhancer/promoter shut-down related events, a result that is consistent with previous results utilizing other modified Ad vectors in vivo (E. Y Ding et. al. in press; Hu et al., *Hum. Gene Ther.* 10:355).

Although the foregoing invention has been described in some detail by way of illustration and example for purposes of clarity and understanding, it will be apparent that certain changes and modifications may be practiced within the scope of the appended claims and equivalents thereof.

What is claimed is:

1. A replicating recombinant adenovirus vector, comprising a replicating recombinant adenovirus vector genome, comprising:
   (a) a heterologous nucleic acid sequence;
   (b) a functional E1 coding region; and
   (b) a mutation in the 100K coding region, such that said adenovirus vector genome has an impairment in 100K activity;
   wherein said adenovirus vector genome is replicated upon introduction into an adenovirus permissive cell.

2. The recombinant adenovirus vector of claim 1, wherein said adenovirus expresses less than about 25% of the 100K activity of an adenovirus with a wild-type 100K coding region.

3. The recombinant adenovirus vector of claim 1, wherein said adenovirus vector genome expresses no detectable 100K activity.

4. The recombinant adenovirus vector of claim 1, wherein said mutation in the 100K coding region comprises a deletion in the 100K coding region.

5. The recombinant adenovirus vector of claim 1, wherein said adenovirus vector may be propagated to produce new adenovirus particles in a cell that expresses a functional 100K protein.

6. The recombinant adenovirus vector of claim 1, wherein said adenovirus vector may be propagated in a transcomplementing cell in the absence of a helper virus.

7. The recombinant adenovirus vector of claim 1, wherein said adenovirus vector genome comprises a deletion in the E3 coding region.

8. The recombinant adenovirus vector of claim 1, wherein said adenovirus vector is a type 2 or type 5 adenovirus vector.

9. The recombinant adenovirus vector of claim 1, wherein said heterologous nucleotide sequence is operatively associated with an expression control sequence.

10. The recombinant adenovirus vector of claim 1, wherein said E1 coding region is operatively associated with a promoter selected from the group consisting of liver-specific, skeletal muscle-specific, cardiac muscle-specific, smooth muscle-specific, diaphragm muscle-specific, prostate-specific, and brain-specific promoters.

11. The recombinant adenovirus vector of claim 1, wherein said E1 coding region is operatively associated with a cancer cell specific promoter.

12. The recombinant adenovirus vector of claim 1, wherein said E1 coding region is operatively associated with an inducible promoter.

13. The recombinant adenovirus vector of claim 1, wherein said heterologous nucleotide sequence encodes a polypeptide.

14. The recombinant adenovirus vector of claim 1, wherein said heterologous nucleotide sequence encodes an antisense RNA, inhibitory RNA or ribozyme.

15. The recombinant adenovirus vector of claim 1, wherein said recombinant adenovirus vector genome is encapsidated within an adenovirus capsid.

16. A cultured cell comprising the replicating recombinant adenovirus vector of claim 1.

17. A method of produing a replicating adenovirus particle, comprising:
   introducing a replicating recombinant adenovirus vector according to claim 1 into a cell that expresses a functional 100K protein under conditions sufficient for replication of the recombinant adenovirus vector genome and packaging of adenovirus particles in the cell; and
   collecting the adenovirus particles.

18. A method of introducing a nucleic acid sequence into a cell, comprising contacting a cell with a replicating recombinant adenovirus vector according to claim 1 under conditions sufficient for entry of the adenovirus particle into the cell.

19. A method of administering a nucleotide sequence to a subject, comprising administering to a subject a replicating recombinant adenovirus vector according to claim 1 in a pharmaceutically acceptable carrier.

20. A method of producing a recombinant adeno-associated virus (AAV) particle, comprising providing to a cell:
   (a) a replicating recombinant adenovirus vector according to claim 1;
   (b) a nucleic acid sequence encoding an AAV vector genome, said AAV vector genome comprising an AAV inverted terminal repeat sequence, a heterologous nucleic acid sequence, and an AAV packaging signal;
   (c) AAV rep coding sequences sufficient for replication of the AAV vector genome;
   (d) AAV cap coding sequences sufficient to produce a functional AAV capsid;
   wherein (a) to (d) are provided to the cell under conditions sufficient for replication and packaging of the AAV vector genome into the AAV capsid,
   whereby AAV particles comprising the AAV vector genome encapsidated within the AAV capsid are produced in the cell.

21. The recombinant adenovirus vector of claim 4, wherein said deletion in the 100K coding region comprises a deletion from about nucleotide 24,990 to about nucleotide 25,687 of the adenovirus serotype 5 genome or a corresponding region of the genome of adenoviruses of other serotypes.

22. The recombinant adenovirus vector of claim 9, wherein said expression control sequence comprises a promoter.

23. The recombinant adenovirus vector of claim 22, wherein said promoter is selected from the group consisting of liver-specific, skeletal muscle-specific, cardiac muscle-specfic, smooth muscle-specific, diaphragm muscle-specific, prostate-specific, and brain-specific promoters.

24. The recombinant adenovirus vector of claim 22, wherein said promoter is a cancer cell specific promoter.

25. The recombinant adenovirus vector of claim 22, wherein said promoter is an inducible promoter.

26. The recombinant adenovirus vector of claim 13, wherein said polypeptide is an industrial enzyme.

27. The recombinant adenovirus vector of claim 13, wherein said polypeptide is an adeno-associated virus capsid protein.

28. The recombinant adenovirus vector of claim 13, wherein said polypeptide is an adeno-assocated virus Rep protein.

29. The recombinant adenovirus vector of claim 13, wherein said polypeptide is an immunogenic polypeptide that induces an immune response against a pathogen.

30. The recombinant adenovirus vector of claim 13, wherein said polypeptide is a reporter potyeptide.

31. The recombinant adenovirus vector of claim 13, wherein said polypeptide is a therapeutic polypeptide.

32. The recombinant adenovirus vector of claim 30, wherein said polypeptide is an anti-cancer agent.

33. A method of producing a polypeptide, comprising:
   introducing the replicating recombinant adenovirus vector of claim 13 into a plurality of cultured cells, under conditions sufficient for the recombinant adenovirus vector to be introduced into the cells and express the encoded polypeptide;
   collecting the polypeptide from the cell culture.

34. The recombinant adenovirus vector of claim 29, wherein said immunogenic polypeptide is a cancer cell immunogen.

35. A method of producing an immune response against a pathogen in a subject, comprising:
   administering to a subject a composition comprising a replicating recombinant adenovirus vector according to claim 29 in a pharmaceutically acceptable carrier;
   wherein the composition is administered in an immunogenically effective amount and under conditions sufficient for the subject to produce an immune response against the pathogen.

36. The recombinant adenovirus vector of claim 31, wherein a deficiency of said polypeptide is associated with a lysosomal storage disease.

37. The recombinant adenovirus vector of claim 31, wherein a deficiency of said polypeptide is associated with a glycogen storage disease.

38. The recombinant adenovirus vector of claim 37, wherein said polypeptide is lysosomal acid α-glucosidase.

39. The cell of claim 16, wherein said cell is a mammalian cell.

40. The cell of claim 16, wherein a nucleic acid sequence encoding a functional adenovirus 100K protein is stably expressed by the cell.

41. A method of treating cancer, comprising
   administering to a subject that has cancer a compostion comprising a replicating recombinant adenovirus vector according to claim 34 in a pharmaceutically acceptable carrier;
   wherein the composition is administered in an immunogenically effective amount and under conditions sufficient for the subject to produce an immune response against the cancer cell immunogen.

42. An isolated nucleic acid sequence comprising a replicating recombinant adenovirus vector genome, comprising:
   (a) a heterologous nucleic acid sequence;
   (b) a functional E1 coding region; and
   (b) a mutation in the 100K coding region, such that said adenovirus vector genome has an impairment in 100K activity;
   wherein said adenovirus vector genome is replicated upon introduction into an adenovirus permissive cell.

43. The isolated nucleic acid sequence of claim 42, wherein said isolated nucleic acid sequence is a plasmid.

44. The method of claim 17, wherein a nucleotide sequence encoding a functional adenovirus 100K protein is stably expressed by the cell.

45. A replicating adenovirus particle produced by the method of claim 17.

46. The method of claim 18, wherein the cell is selected from the group consisting of a neuron, a brain cell, a retinal cell, an epithelial cell, a cardiac muscle cell, a smooth muscle cell, a skeletal muscle cell, a diaphragm muscle cell, a pancreatic cell, a liver cell, a fibroblast, an endothelial cell, a germ cell, a lung cell, a prostate cell, a stem cell, and a progenitor cell.

47. The method of claim 18, wherein the cell is a cancer cell.

48. The method of claim 18, wherein the cell is a mammalian cell.

49. The method of claim 18, wherein the adenovirus vector genome is replicated in the cell.

50. The method of claim 18, wherein the cell does not provide a functional 100K protein.

51. A method of administering a nucleotide sequence to a subject, comprising administering to a subject a cell produced by the method according to claim 18 in a pharmaceutically acceptable carrier.

52. The method of claim 50, wherein accumulation of an adenovirus late gene product in the cell is reduced as compared with an adenovirus vector that expresses a functional 100K protein.

53. The method of claim 19, wherein the subject is selected from the group consisting of avian subjects and mammalian subjects.

54. The method of claim 19, wherein the subject has cancer.

55. The method of claim 53, wherein the subject is a mammalian subject.

56. The method of claim 55, wherein the subject is a human subject.

57. The method of claim 55, wherein the recombinant adenovirus vector is administered by a route selected from the group consisting of oral, rectal, transmucosal, transdermal, inhalation, intravenous, subcutaneous, intradermal, intramuscular, and intraarticular administration.

58. The method of claim 55, wherein the recombinant adenovirus vector is administered to the liver.

59. The method of claim 55, wherein the recombinant adenovirus vector is injected directly into a cancerous tissue.

60. The method of claim 55, wherein a therapeutic effect is achieved at a lower viral dose than with a non-replicating adenovirus vector.

61. The method of claim 19 or claim 50, wherein the subject has been diagnosed with lysosomal acid α-glucosidase deficiency.

62. The method of claim 59, wherein the recombinant adenovirus vector is delivered to the liver by a method selected from the group consisting of intravenous administration, intraportal administration, intrabiliary administration, intra-arterial administration, and direct injection into the liver parenchyma.

63. The method of claim 33, wherein the plurality of cultured cells are mammalian cells.

64. The method of claim 20, further comprising the step of collecting the recombinant AAV particles.

65. The method of claim 20, wherein the adenovirus vector genome comprises AAV cap sequences.

66. The method of claim 20, wherein the adenovirus vector genome comprises AAV rep sequences.

67. The method of claim 20, further comprising providing to the cell the adenovirus helper functions for AAV replication and packaging.

68. The method of claim 20, wherein the AAV inverted terminal repeats and the AAV capsid are derived from different AAV serotypes.

69. The method of claim 20, wherein the AAV capsid is an AAV-6 capsid.

70. The method of claim 20, wherein the AAV inverted terminal repeats are AAV-2 inverted terminal repeats.

* * * * *

UNITED STATES PATENT AND TRADEMARK OFFICE
CERTIFICATE OF CORRECTION

PATENT NO.        : 6,946,126 B2
APPLICATION NO. : 10/159946
DATED             : September 20, 2005
INVENTOR(S)       : Amalfitano et al.

It is certified that error appears in the above-identified patent and that said Letters Patent is hereby corrected as shown below:

Column 36,
Line 5 should read -- wherein said polypeptide is a reporter polypeptide. --

Line 8 should read -- 32. The recombinant adenovirus vector of claim 13, --

Column 38,
Line 10 should read -- 61. The method of claim 19 or 56, wherein the --

Line 13 should read -- 62. The method of claim 58, wherein the recombinant --

Signed and Sealed this

Twelfth Day of September, 2006

JON W. DUDAS
*Director of the United States Patent and Trademark Office*